(12) United States Patent
Yao et al.

(10) Patent No.: US 9,743,885 B1
(45) Date of Patent: Aug. 29, 2017

(54) METHOD OF TWO-STEP PARYLENE PATTERNING AND ETCHING TO RELEASE A PARYLENE SANDWICHED DEVICE

(71) Applicant: Verily Life Sciences LLC, Mountain View, CA (US)

(72) Inventors: Huanfen Yao, Sunnyvale, CA (US); James Etzkorn, Mountain View, CA (US); Harvey Ho, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 380 days.

(21) Appl. No.: 14/302,844

(22) Filed: Jun. 12, 2014

(51) Int. Cl.
| | |
|---|---|
| *H05K 3/30* | (2006.01) |
| *A61B 5/00* | (2006.01) |
| *A61B 5/1486* | (2006.01) |
| *A61B 3/10* | (2006.01) |
| *A61B 17/00* | (2006.01) |

(52) U.S. Cl.
CPC ............ *A61B 5/6821* (2013.01); *A61B 3/101* (2013.01); *A61B 5/1486* (2013.01); *A61B 2017/00526* (2013.01)

(58) Field of Classification Search
CPC . A61B 3/101; A61B 5/14507; A61B 5/14532; A61B 5/14546; A61B 5/1486; A61B 5/6821
USPC .................................................. 29/832, 846
See application file for complete search history.

(56) References Cited

U.S. PATENT DOCUMENTS

| | | | |
|---|---|---|---|
| 8,096,654 B2 | 1/2012 | Amirparviz et al. | |
| 8,529,538 B2 | 9/2013 | Pang et al. | |
| 8,536,667 B2 | 9/2013 | de Graff et al. | |
| 8,608,310 B2 | 12/2013 | Otis | |
| 9,009,958 B2* | 4/2015 | Etzkorn | G02C 7/083 |
| | | | 29/832 |
| 9,044,200 B1* | 6/2015 | Liu | A61B 5/6832 |

(Continued)

OTHER PUBLICATIONS

Patel, Jasbir N., Bonnie L. Gray, Bozena Kaminska, and Byron D. Gates, "Flexible glucose sensor utilizing multilayer PDMS process," In Engineering in Medicine and Biology Society, 2008. EMBS 2008. 30th Annual International Conference of the IEEE, pp. 5749-5752, 2008.

(Continued)

*Primary Examiner* — Paul D Kim
(74) *Attorney, Agent, or Firm* — McDonnell Boehnen Hulbert & Berghoff LLP

(57) ABSTRACT

An example method involves: forming a first bio-compatible layer that defines a first side of a bio-compatible device; forming a conductive pattern over a portion of the first bio-compatible layer; mounting an electronic component to the electrical contacts; forming a second bio-compatible layer over the first bio-compatible layer, the electronic component, the conductive pattern, wherein the second bio-compatible layer defines a second side of the bio-compatible device; forming a first etch mask to partially cover the second bio-compatible layer, thereby exposing a first portion of the second bio-compatible layer; removing the first portion of the second bio-compatible layer; forming a second etch mask to partially cover the second bio-compatible layer, thereby exposing a second portion of the second bio-compatible layer; and removing the second portion of the second bio-compatible layer.

16 Claims, 12 Drawing Sheets

(56) References Cited

U.S. PATENT DOCUMENTS

| | | | |
|---|---|---|---|
| 9,113,829 B2* | 8/2015 | Etzkorn | G02C 7/083 |
| 9,282,920 B2* | 3/2016 | Ho | A61B 5/14503 |
| 2012/0302861 A1 | 11/2012 | Marshall et al. | |
| 2013/0302398 A1 | 11/2013 | Ambati et al. | |
| 2015/0173680 A1* | 6/2015 | Etzkorn | A61B 5/6821 |
| | | | 600/345 |

OTHER PUBLICATIONS

Yao, Huanfen, et al., "A Contact Lens With Embedded Sensor for Monitoring Tear Glucose Level," Biosensors and Bioelectronics 26.7: 3290-3296, 2011.

\* cited by examiner

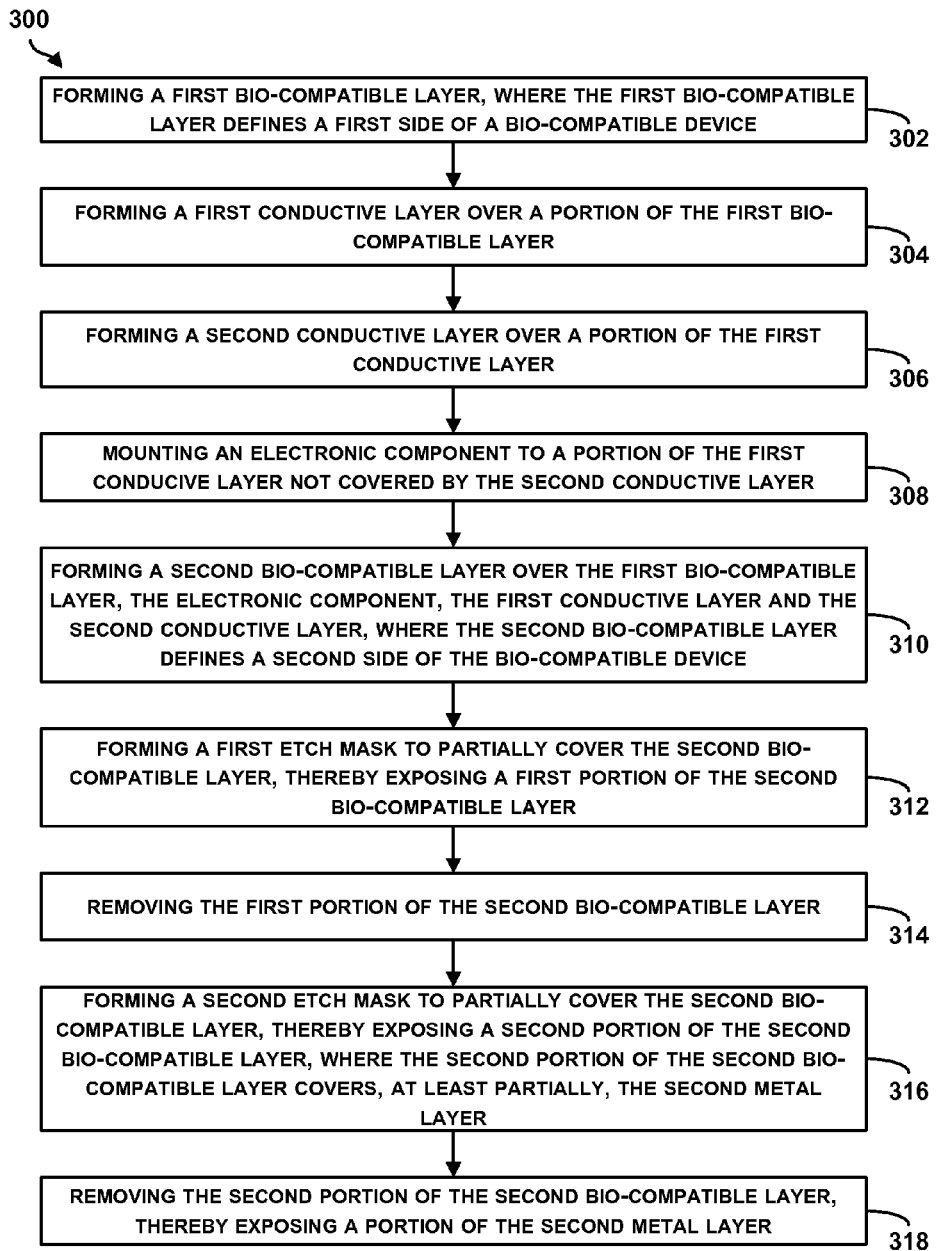

METHOD OF TWO-STEP PARYLENE PATTERNING AND ETCHING TO RELEASE A PARYLENE SANDWICHED DEVICE

BACKGROUND

Unless otherwise indicated herein, the materials described in this section are not prior art to the claims in this application and are not admitted to be prior art by inclusion in this section.

A body-mountable device may be configured to monitor health-related information based on at least one analyte from a user. For example, a bio-compatible device may be embedded in a polymer to provide the body-mountable device. The bio-compatible device could include, for example, a sensor configured to detect the at least one analyte (e.g., glucose) in a fluid of a user wearing the body-mountable device. The body-mountable device may also be configured to monitor various other types of health-related information.

SUMMARY

The present disclosure describes embodiments that relate to a method of two-step parylene patterning and etching to release a parylene sandwiched device. In one aspect, the present application describes a method. The method includes forming a first bio-compatible layer, where the first bio-compatible layer defines a first side of a bio-compatible device. The method also includes forming a first conductive layer over a portion of the first bio-compatible layer, and forming a second conductive layer over a portion of the first conductive layer. The method further includes mounting an electronic component to a portion of the first conductive layer not covered by the second conductive layer. The method also includes forming a second bio-compatible layer over the first bio-compatible layer, the electronic component, the first conductive layer and the second conductive layer. The second bio-compatible layer defines a second side of the bio-compatible device. The method further includes forming a first etch mask to partially cover the second bio-compatible layer, thereby exposing a first portion of the second bio-compatible layer. The method also includes removing the first portion of the second bio-compatible layer. The method further includes forming a second etch mask to partially cover the second bio-compatible layer, thereby exposing a second portion of the second bio-compatible layer. The second portion of the second bio-compatible layer covers, at least partially, the second conductive layer. The method also includes removing the second portion of the second bio-compatible layer, thereby exposing a portion of the second conductive layer.

In another aspect, the present disclosure describes another method. The method includes forming a first bio-compatible layer, where the first bio-compatible layer defines a first side of a bio-compatible device. The method also includes forming a conductive pattern over a portion of the first bio-compatible layer. The conductive pattern defines an antenna, sensor electrodes, electrical contacts, and one or more electrical interconnects. The method further includes mounting an electronic component to the electrical contacts. The method also includes forming a second bio-compatible layer over the first bio-compatible layer, the electronic component, the conductive pattern, where the second bio-compatible layer defines a second side of the bio-compatible device. The method further includes forming a first etch mask to partially cover the second bio-compatible layer, thereby exposing a first portion of the second bio-compatible layer. The method also includes removing the first portion of the second bio-compatible layer. The method further includes forming a second etch mask to partially cover the second bio-compatible layer, thereby exposing a second portion of the second bio-compatible layer, where the second portion of the second bio-compatible layer covers the sensor electrode. The method also includes removing the second portion of the second bio-compatible layer, thereby exposing the sensor electrodes.

In still another aspect, the present disclosure describes a bio-compatible device. The bio-compatible device includes a first bio-compatible layer, where the first bio-compatible layer defines a first side of the bio-compatible device. The bio-compatible device also includes a conductive pattern formed over a portion of the first bio-compatible layer, where the conductive pattern defines an antenna, sensor electrodes, electrical contacts, and one or more electrical interconnects. The bio-compatible device further includes an electronic component mounted to the electrical contacts. The bio-compatible device also includes a second bio-compatible layer formed over the first bio-compatible layer, the electronic component, the conductive pattern. The second bio-compatible layer defines a second side of the bio-compatible device. The second bio-compatible layer has an opening that exposes a portion of the conductive pattern, where the opening is formed by etching through the second bio-compatible layer to the conductive pattern The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 3 is a flow chart of a method of two-step parylene patterning and etching to release a parylene sandwiched device, in accordance with an example embodiment.

DETAILED DESCRIPTION

The following detailed description describes various features and functions of the disclosed systems and methods with reference to the accompanying figures. In the figures, similar symbols identify similar components, unless context dictates otherwise. The illustrative system and method embodiments described herein are not meant to be limiting. It may be readily understood that certain aspects of the disclosed systems and methods can be arranged and combined in a wide variety of different configurations, all of which are contemplated herein.

I. EXAMPLE SYSTEMS AND DEVICES

A bio-compatible device may include a first bio-compatible layer, a conductive pattern on the first bio-compatible layer, an electronic component mounted to the conductive pattern, and a second bio-compatible layer over the first bio-compatible layer, the electronic component, and the conductive pattern.

An example body-mountable device that comprises an eye-mountable device that is configured to detect at least one analyte in a tear film of a user wearing the eye-mountable device will now be described in greater detail.

Figure 1:
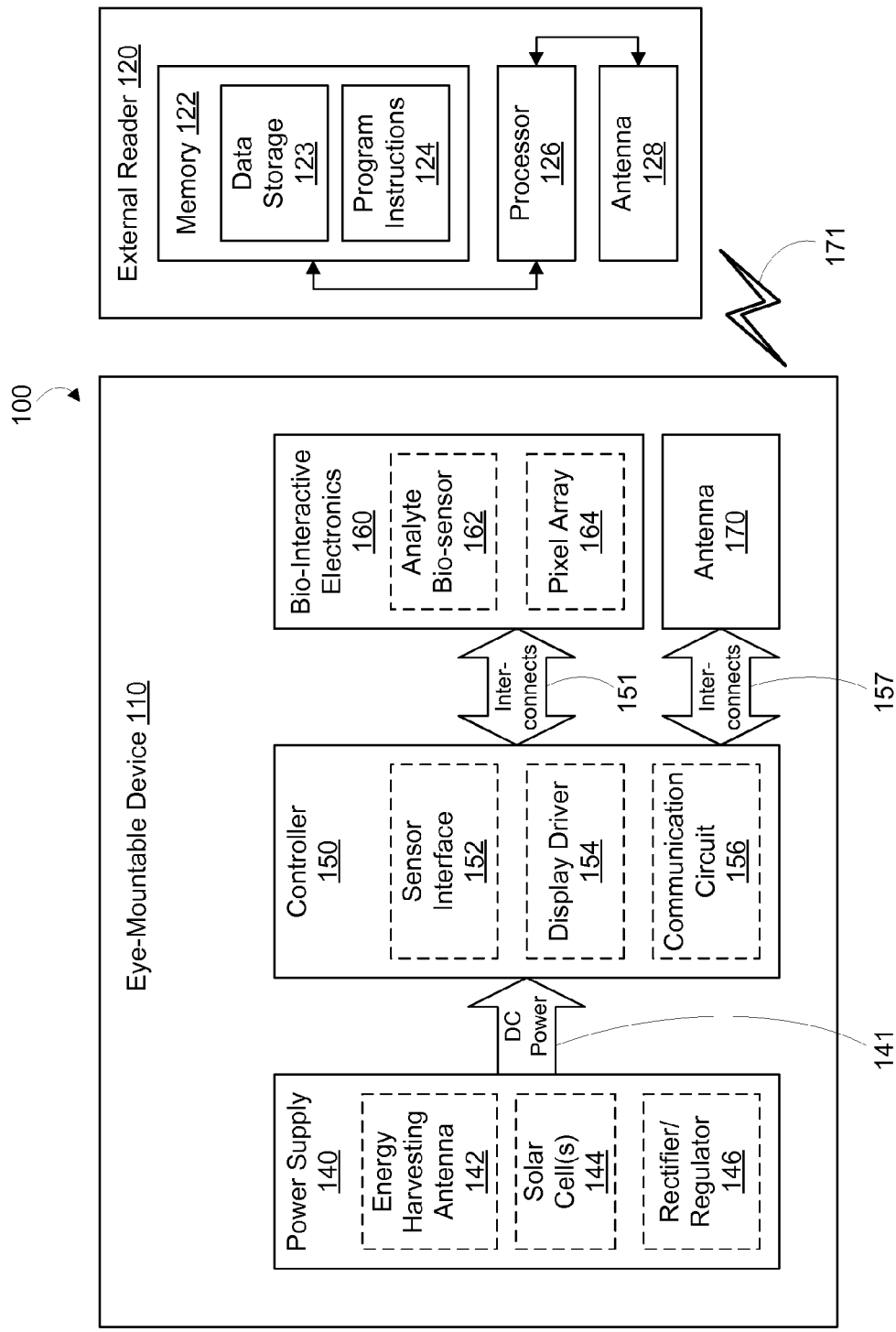
FIG. 1 is a block diagram of a system with an eye-mountable device in wireless communication with an external reader, in accordance with an example embodiment.

FIG. 1 is a block diagram of a system 100 that includes an eye-mountable device 110 in wireless communication with an external reader 120. The eye-mountable device 110 may be a polymeric material that may be appropriately shaped for mounting to a corneal surface and in which a structure is at least partially embedded. The structure may include a power supply 140, a controller 150, bio-interactive electronics 160, and an antenna 170.

In some examples, the structure may be a bio-compatible device in which some or all of the components formed or mounted thereon are encapsulated by a bio-compatible material.

In some examples, the structure may be positioned away from the center of the eye-mountable device 110 and thereby avoid interference with light transmission to the central, light-sensitive region of the eye. For example, where the eye-mountable device 110 is shaped as a curved disk, the structure may be embedded around the periphery (e.g., near the outer circumference) of the disk. In other examples, the structure may be positioned in or near the central region of the eye-mountable device 110. For example, portions of the structure may be substantially transparent to incoming visible light to mitigate interference with light transmission to the eye. Moreover, in some examples, the bio-interactive electronics 160 may include a pixel array 164 that emits and/or transmits light to be received by the eye according to display instructions. Thus, the bio-interactive electronics 160 may optionally be positioned in the center of the eye-mountable device so as to generate visual cues perceivable to a wearer of the eye-mountable device 110, such as displaying information (e.g., characters, symbols, flashing patterns, etc.) on the pixel array 164.

The power supply 140 is configured to harvest ambient energy to power the controller 150 and bio-interactive electronics 160, and may include an energy harvesting antenna 142 and/or solar cells 144. The energy harvesting antenna 142 may capture energy from incident radio radiation. The solar cells 144 may comprise photovoltaic cells configured to capture energy from incoming ultraviolet, visible, and/or infrared radiation.

A rectifier/regulator 146 may be used to condition the captured energy to a stable DC supply voltage 141 at a level suitable for operating the controller, and then supply the voltage to the controller 150. The rectifier/regulator 146 may include one or more energy storage devices to mitigate high frequency variations in the energy harvesting antenna 142 and/or solar cell(s) 144. For example, one or more energy storage devices (e.g., a capacitor or an inductor) may be connected in parallel across the outputs of the rectifier/regulator 146 to regulate the DC supply voltage 141 and may be configured to function as a low-pass filter.

The controller 150 is configured to execute instructions to operate the bio-interactive electronics 160 and the antenna 170. The controller 150 includes logic circuitry configured to operate the bio-interactive electronics 160 so as to interact with a biological environment of the eye-mountable device 110. The interaction could involve the use of one or more components, such an analyte bio-sensor 162 in the bio-interactive electronics 160, to obtain input from the biological environment. Additionally or alternatively, the interaction could involve the use of one or more components, such as a pixel array 164, to provide an output to the biological environment.

In one example, the controller 150 includes a sensor interface module 152 that is configured to operate the analyte bio-sensor 162. The analyte bio-sensor 162 may be, for example, an amperometric electrochemical sensor that includes a working electrode and a reference electrode driven by a sensor interface. A voltage is applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current can be dependent on the analyte concentration. Thus, the amount of the amperometric current that is measured through the working electrode can provide an indication of analyte concentration. In some examples, the sensor interface module 152 can be a potentiostat configured to apply a voltage difference between working and reference electrodes while measuring a current through the working electrode.

In some instances, a reagent may also be included to sensitize the electrochemical sensor to one or more desired analytes. For example, a layer of glucose oxidase ("GOD") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

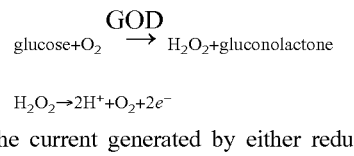

$$H_2O_2 \rightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 may also include a display driver module 154 for operating a pixel array 164. The pixel array 164 is an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 may also include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 may also include a communication circuit 156 for sending and/or receiving information via the antenna 170. The communication circuit 156 may include one or more oscillators, mixers, frequency injectors, or the like to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 120. For example, the communication circuit 156 can cause variations in the amplitude, phase, and/or frequency of backscatter radiation from the antenna 170, and such variations may then be detected by the reader 120.

The controller 150 is connected to the bio-interactive electronics 160 via interconnects 151. Similarly, the controller 150 is connected to the antenna 170 via interconnects 157. The interconnects 151, 157 may comprise a patterned conductive material (e.g., gold, platinum, palladium, titanium, copper, aluminum, silver, metals, any combinations of these, etc.).

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component.

Additionally or alternatively, the energy harvesting antenna 142 and the antenna 170 can be implemented in the same, dual-purpose antenna. For example, a loop antenna can both harvest incident radiation for power generation and communicate information via backscatter radiation.

The external reader 120 includes an antenna 128 (or group of more than one antennae) to send and receive wireless signals 171 to and from the eye-mountable device 110. The external reader 120 also includes a computing system with a processor 126 in communication with a memory 122. The memory 122 is a non-transitory computer-readable medium that can include, without limitation, magnetic disks, optical disks, organic memory, and/or any other volatile (e.g., RAM) or non-volatile (e.g., ROM) storage system readable by the processor 126. The memory 122 includes a data storage 123 to store indications of data, such as sensor readings (e.g., from the analyte bio-sensor 162), program settings (e.g., to adjust behavior of the eye-mountable device 110 and/or external reader 120), etc. The memory 122 also includes program instructions 124 for execution by the processor 126. For example, the program instructions 124 may cause the external reader 120 to provide a user interface that allows for retrieving information communicated from the eye-mountable device 110 (e.g., sensor outputs from the analyte bio-sensor 162). The external reader 120 may also include one or more hardware components for operating the antenna 128 to send and receive the wireless signals 171 to and from the eye-mountable device 110. For example, oscillators, frequency injectors, encoders, decoders, amplifiers, and filters can drive the antenna 128 according to instructions from the processor 126.

The external reader 120 may be a smart phone, digital assistant, or other portable computing device with wireless connectivity sufficient to provide the wireless communication link 171. The external reader 120 may also be implemented as an antenna module that can be plugged in to a portable computing device, such as in an example where the communication link 171 operates at carrier frequencies not commonly employed in portable computing devices. In some instances, the external reader 120 is a special-purpose device configured to be worn relatively near a wearer's eye to allow the wireless communication link 171 to operate using little or low power. For example, the external reader 120 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. To perform a reading with the system 100 configured as a tear film analyte monitor, the external reader 120 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 141 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 120 (e.g., via the communication circuit 156).

In some examples, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 120 to the eye-mountable device 110 to request a measurement. By periodically interrogating the eye-mountable device 110 (e.g., by supplying radio frequency radiation 171 to temporarily turn the device on) and storing the sensor results (e.g., via the data storage 123), the external reader 120 can accumulate a set of analyte concentration measurements over time without continuously powering the eye-mountable device 110.

Figure 2A:
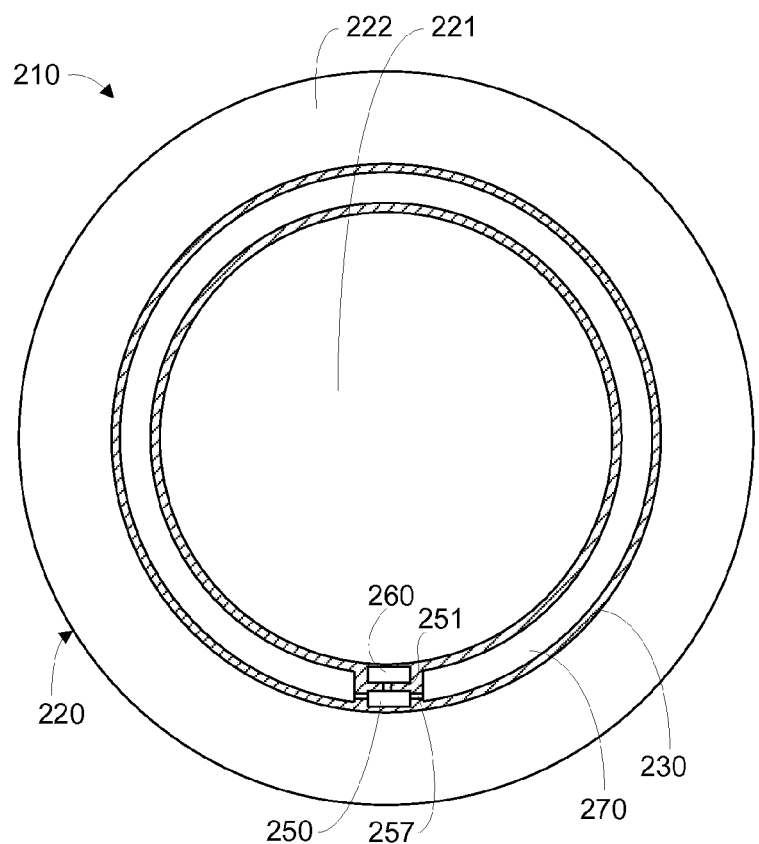
FIG. 2A is a top view of an eye-mountable device, in accordance with an example embodiment.
Figure 2B:
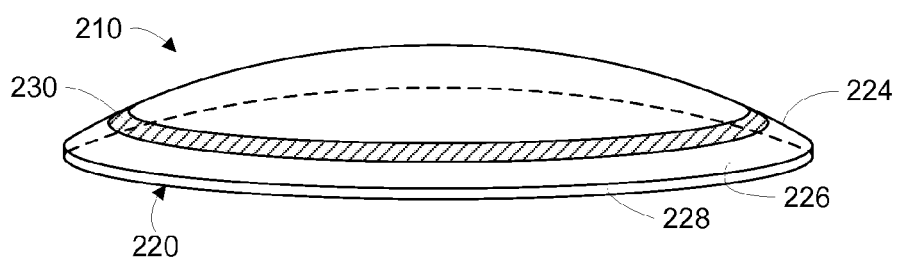
FIG. 2B is a side view of an eye-mountable device, in accordance with an example embodiment.

FIG. 2A is a top view of an eye-mountable device 210. FIG. 2B is side view of the eye-mountable device 210. It is noted that relative dimensions in FIGS. 2A and 2B are not necessarily to scale, but have been rendered for purposes of explanation only in describing the arrangement of the eye-mountable device 210.

The eye-mountable device 210 may include a polymeric material 220, which may be a substantially transparent material to allow incident light to be transmitted to the eye. The polymeric material 220 may include one or more bio-compatible materials similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, or any combinations of these. Other polymeric materials may also be envisioned. The polymeric material 220 may include materials configured to moisturize the corneal surface, such as hydrogels and the like. In some examples, the polymeric material 220 is a deformable ("non-rigid") material to enhance wearer comfort.

To facilitate contact-mounting, the eye-mountable device 210 may comprise a concave surface 226 configured to adhere ("mount") to a moistened corneal surface (e.g., by capillary forces with a tear film coating the corneal surface). While mounted with the concave surface against the eye, a convex surface 224 of eye-mountable device 210 is formed so as not to interfere with eye-lid motion while the eye-mountable device 210 is mounted to the eye. A circular outer side edge 228 connects the convex surface 224 and the concave surface 226. The convex surface 224 can therefore be considered an outer, top surface of the eye-mountable device 210 whereas the concave surface 226 can be considered an inner, bottom surface. The "top" view shown in FIG. 2a is facing the convex surface 224.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some examples, the dimensions of the eye-mountable device 210 may be selected according to the size and/or shape of the corneal surface and/or the scleral surface of the wearer's eye. In some examples, the eye-mountable device 210 is shaped to provide a predetermined, vision-correcting optical power, such as provided by a prescription contact lens.

A structure 230 is embedded in the eye-mountable device 210. The structure 230 can be embedded to be situated near or along an outer periphery 222, away from a central region 221. Such a position ensures that the structure 230 will not interfere with a wearer's vision when the eye-mountable device 210 is mounted on a wearer's eye, because it is positioned away from the central region 221 where incident light is transmitted to the light-sensing portions of the eye. Moreover, portions of the structure 230 can be formed of a transparent material to further mitigate effects on visual perception.

The structure 230 may be shaped as a flat, circular ring (e.g., a disk with a centered hole). The flat surface of the structure 230 (e.g., along the radial width) allows for mounting electronics such as chips (e.g., via flip-chip mounting) and for patterning conductive materials to form electrodes, antenna(e), and/or interconnections. The structure 230 and the polymeric material 220 may be approximately cylindrically symmetric about a common central axis. The structure 230 may have, for example, a diameter of about 10 millimeters, a radial width of about 1 millimeter (e.g., an outer radius 1 millimeter greater than an inner radius), and a thickness of about 50 micrometers. These dimensions are provided for example purposes only, and in no way limit this disclosure.

A loop antenna 270, controller 250, and bio-interactive electronics 260 are included in the structure 230. The controller 250 may be a chip including logic elements configured to operate the bio-interactive electronics 260 and the loop antenna 270. The controller 250 is electrically connected to the loop antenna 270 by interconnects 257 also situated on the structure 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) may be formed from any type of conductive material and may be patterned by any process that can be used for patterning such materials, such as deposition or photolithography, for example. The conductive materials patterned on the structure 230 may be, for example, gold, platinum, palladium, titanium, carbon, aluminum, copper, silver, silver-chloride, conductors formed from noble materials, metals, or any combinations of these materials. Other materials may also be envisioned.

The structure 230 may be a bio-compatible device in which some or all of the components are encapsulated by a bio-compatible material. In one example, the controller 250, interconnects 251, 257, bio-interactive electronics 260, and the loop antenna 270 are fully encapsulated by bio-compatible material, except for the sensor electrodes in the bio-interactive electronics 260.

Figure 2D:
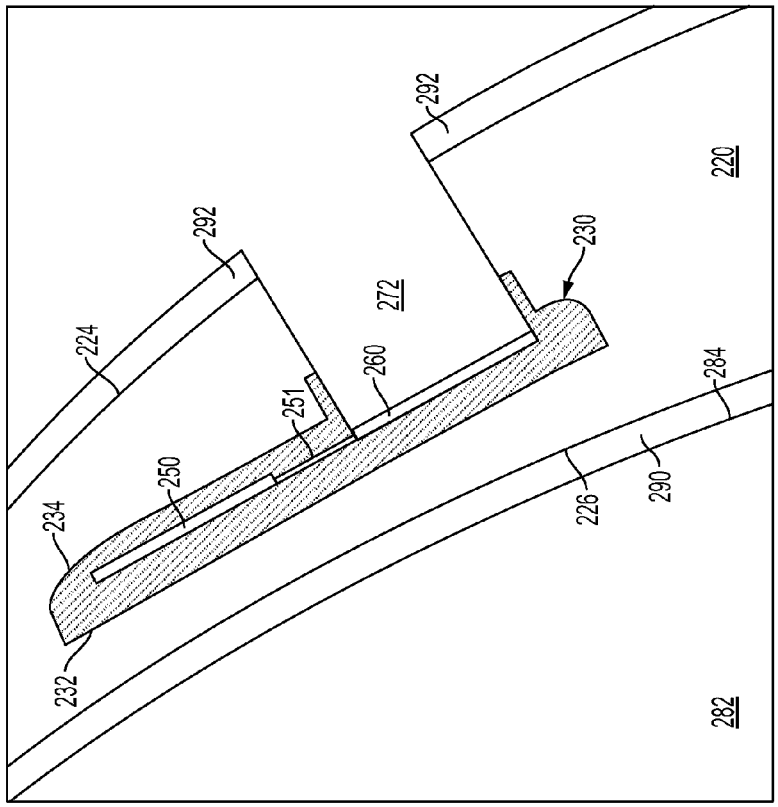
FIG. 2D is a side cross-section view showing the tear film layers surrounding the surfaces of the eye-mountable device mounted as shown in FIG. 2C, in accordance with an example embodiment.

As shown in FIG. 2A, the bio-interactive electronics module 260 is on a side of the structure 230 facing the convex surface 224. Where the bio-interactive electronics module 260 includes an analyte bio-sensor, for example, mounting such a bio-sensor on the structure 230 to be close to the convex surface 224 allows the bio-sensor to sense analyte that has diffused through convex surface 224 or has reached the bio-sensor through a channel in the convex surface 224 (FIGS. 2C and 2D show a channel 272).

The loop antenna 270 is a layer of conductive material patterned along the flat surface of the structure 230 to form a flat conductive ring. In some examples, the loop antenna 270 does not form a complete loop. For example, the loop antenna 270 may include a cutout to allow room for the controller 250 and bio-interactive electronics 260, as illustrated in FIG. 2A. However, in another example, the loop antenna 270 can be arranged as a continuous strip of conductive material that wraps entirely around the structure 230 one or more times. Interconnects between the ends of such a wound antenna (e.g., the antenna leads) can connect to the controller 250 in the structure 230. In some examples, the loop antenna can include a plurality of conductive loops spaced apart from each other, such as three conductive loops, five conductive loops, nine conductive loops, etc. With such an arrangement, the polymeric material 220 may extend between adjacent conductive loops in the plurality of conductive loops.

Figure 2C:
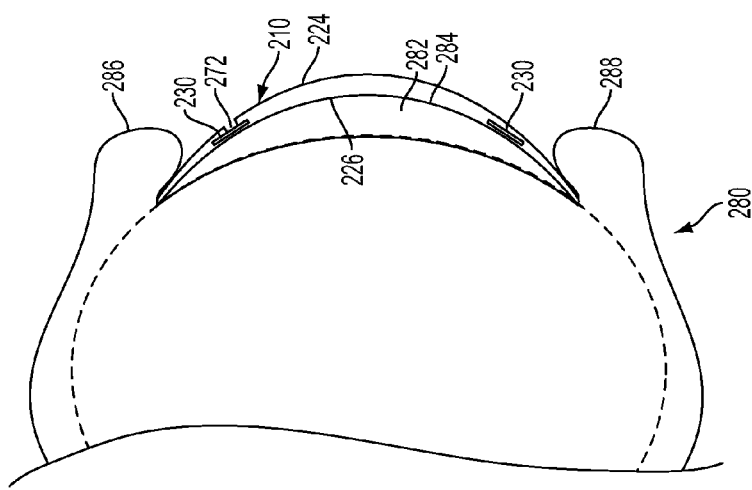
FIG. 2C is a side cross-section view of the eye-mountable device of FIG. 2A while mounted to a corneal surface of the eye, in accordance with an example embodiment.

FIG. 2C is a side cross-section view of the eye-mountable electronic device 210 mounted to a corneal surface 284 of an eye 280. FIG. 2D is an enlarged partial view of the cross-section of the eye-mountable device shown in FIG. 2C. It is noted that relative dimensions in FIGS. 2C and 2D are not necessarily to scale, but have been rendered for purposes of explanation only in describing the arrangement of the eye-mountable device 210. Some aspects are exaggerated to allow for illustration and to facilitate explanation.

The eye 280 includes a cornea 282 that is covered by bringing an upper eyelid 286 and a lower eyelid 288 together over the surface of the eye 280. Incident light is received by the eye 280 through the cornea 282, where light is optically directed to light sensing elements of the eye 280 to stimulate visual perception. The motion of the upper and lower eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the convex and concave surfaces 224, 226, providing an inner layer 290 (along the concave surface 226) and an outer layer 292 (along the convex surface 224). The inner layer 290 on the corneal surface 284 also facilitates mounting the eye-mountable device 210 by capillary forces between the concave surface 226 and the corneal surface 284. In some examples, the eye-mountable device 210 can also be held over the eye 280 in part by vacuum forces against the corneal surface 284 due to the curvature of the concave surface 226. The tear film layers 290, 292 may be about 10 micrometers in thickness and together account for about 10 microliters of fluid.

The tear film is in contact with the blood supply through capillaries in the structure of the eye and includes many biomarkers found in blood that are analyzed to diagnose health states of an individual. For example, tear film includes glucose, calcium, sodium, cholesterol, potassium, other biomarkers, etc. The biomarker concentrations in tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body.

As shown in the cross-sectional views in FIGS. 2C and 2D, the structure 230 can be inclined so as to be approximately parallel to the adjacent portion of the convex surface 224. As described above, the structure 230 is a flattened ring with an inward-facing surface 232 (closer to the concave surface 226 of the polymeric material 220) and an outward-facing surface 234 (closer to the convex surface 224). The structure 230 can include electronic components and/or patterned conductive materials adjacent to either or both surfaces 232, 234.

As shown in FIG. 2D, the bio-interactive electronics 260, the controller 250, and the conductive interconnect 251 are located between the outward-facing surface 234 and the inward-facing surface 232 such that the bio-interactive electronics 260 are facing the convex surface 224. With this arrangement, the bio-interactive electronics 260 can receive analyte concentrations in the tear film 292 through the channel 272. However, in other examples, the bio-interactive electronics 260 may be mounted on the inward-facing surface 232 of the structure 230 such that the bio-interactive electronics 260 are facing the concave surface 226.

While the body-mountable device has been described as comprising the eye-mountable device 110 and/or the eye-mountable device 210, the body-mountable device could comprise other mountable devices that are mounted on or in other portions of the human body.

For example, in some examples, the body-mountable device may comprise a tooth-mountable device. In some examples, the tooth-mountable device may take the form of or be similar in form to the eye-mountable device 110 and/or the eye-mountable device 210. For instance, the tooth-mountable device could include a polymeric material that is the same as or similar to any of the polymeric materials described herein and a structure that is the same as or similar to any of the structures described herein. With such an arrangement, the tooth-mountable device may be configured to detect at least one analyte in a fluid (e.g., saliva) of a user wearing the tooth-mountable device.

Moreover, in some examples, the body-mountable device may comprise a skin-mountable device. In some examples, the skin-mountable device may take the form of or be similar in form to the eye-mountable device 110 and/or the eye-mountable device 210. For instance, the skin-mountable device could include a polymeric material that is the same as or similar to any of the polymeric materials described herein and a structure that is the same as or similar to any of the structures described herein. With such an arrangement, the skin-mountable device may be configured to detect at least one analyte in a fluid (e.g., perspiration, blood, etc.) of a user wearing the skin-mountable device.

Further, some examples may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

II. EXAMPLE METHODS

FIG. 3 is a flow chart of a method 300 of two-step parylene patterning and etching to release a parylene sandwiched device, in accordance with an example embodiment. The method 300 may include one or more operations, functions, or actions as illustrated by one or more of blocks 302-318. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

Figure 4A:
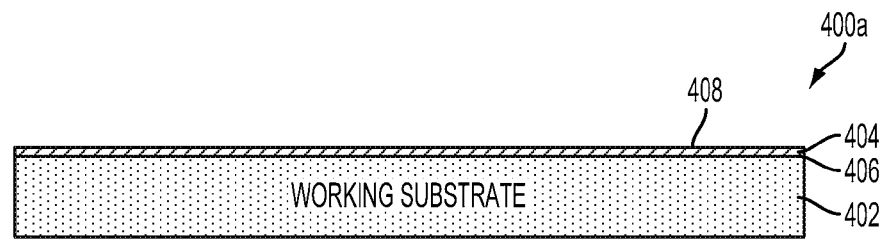
FIGS. 4A-4T illustrates stages of fabricating a bio-compatible device, in accordance with an example embodiment.
Figure 4B:
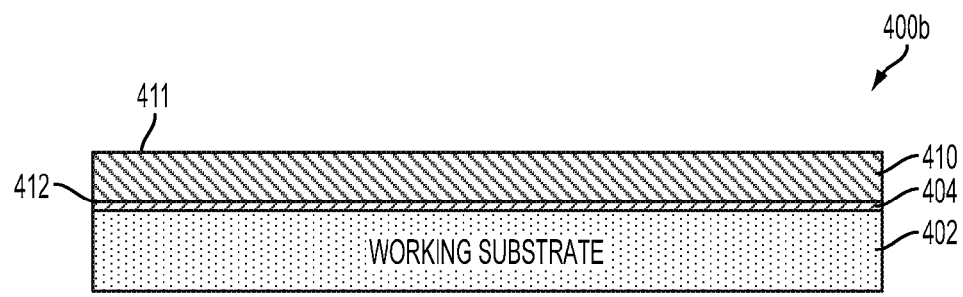
Figure 4C:
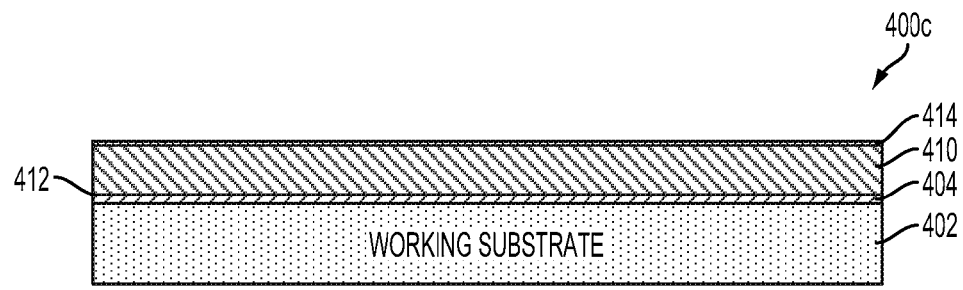
Figure 4D:
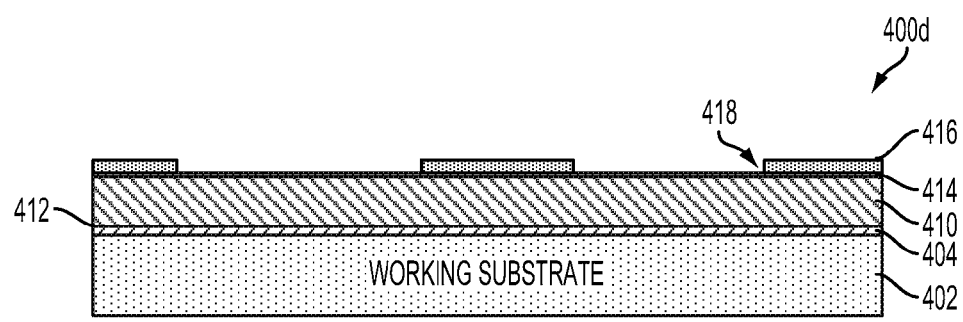
Figure 4E:
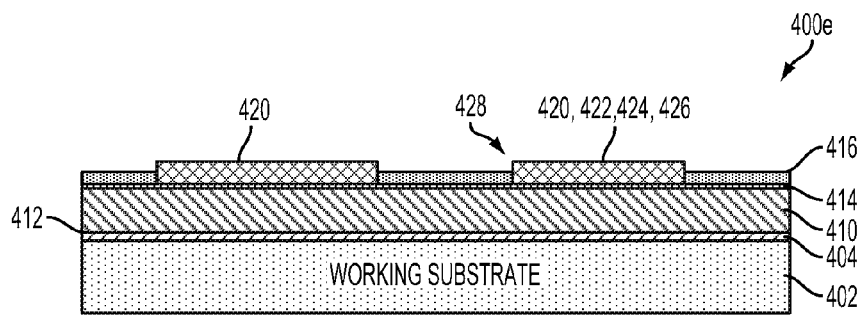
Figure 4F:
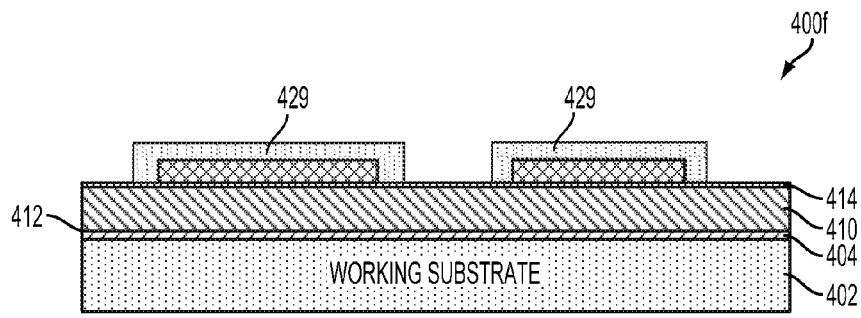
Figure 4G:
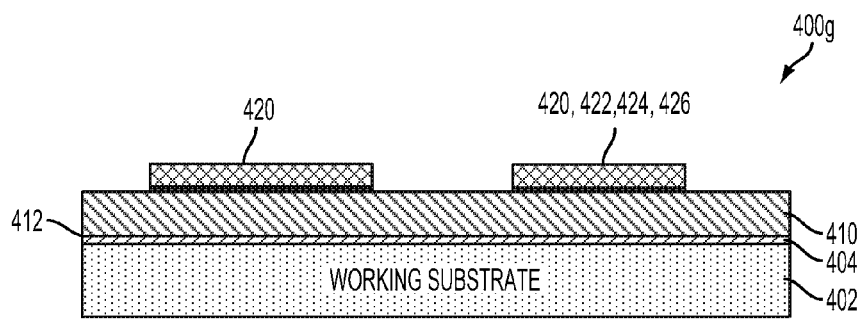
Figure 4H:
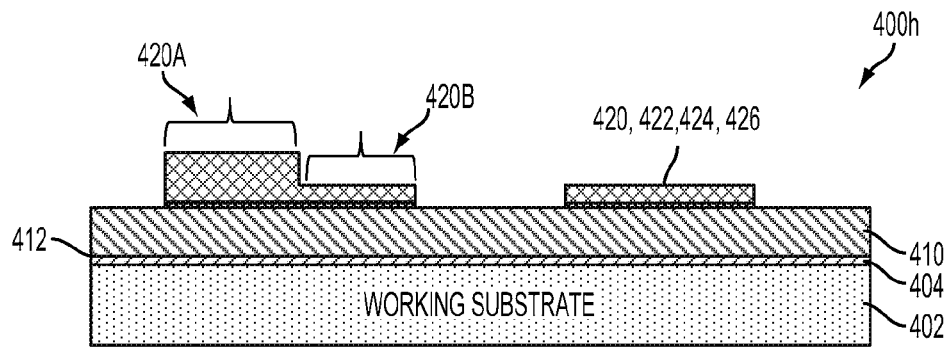
Figure 4I:
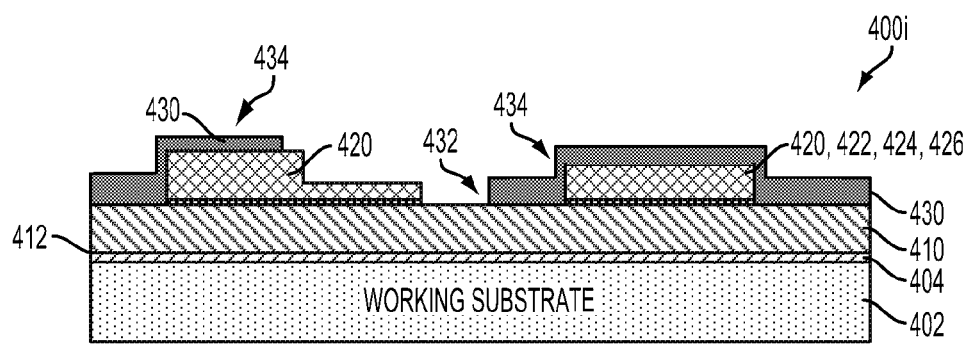
Figure 4J:
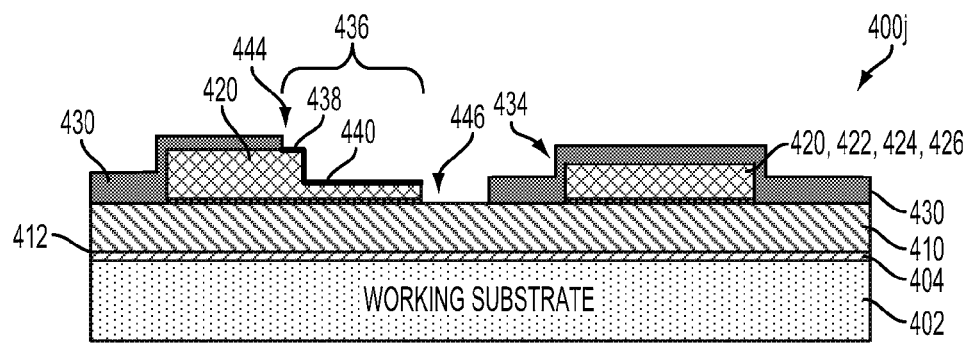
Figure 4K:
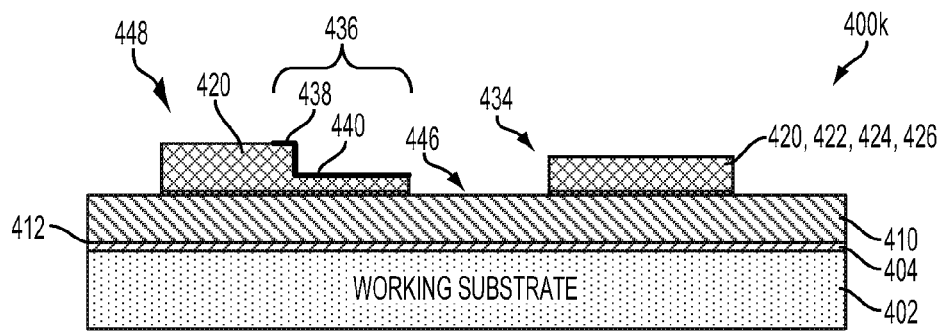
Figure 4L:
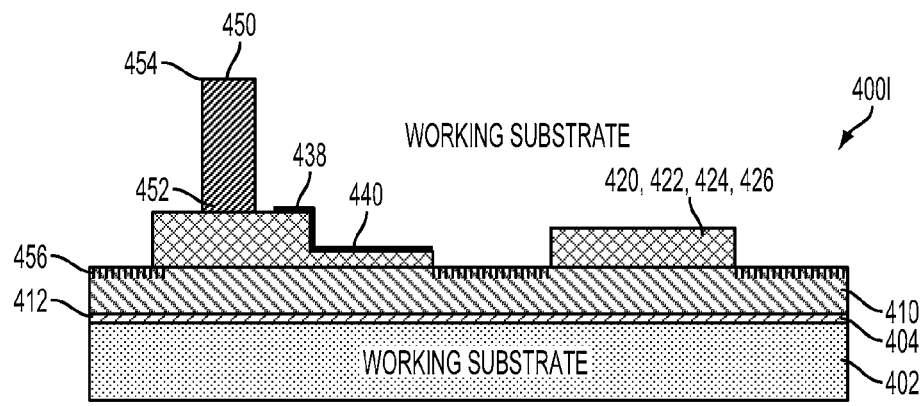
Figure 4M:
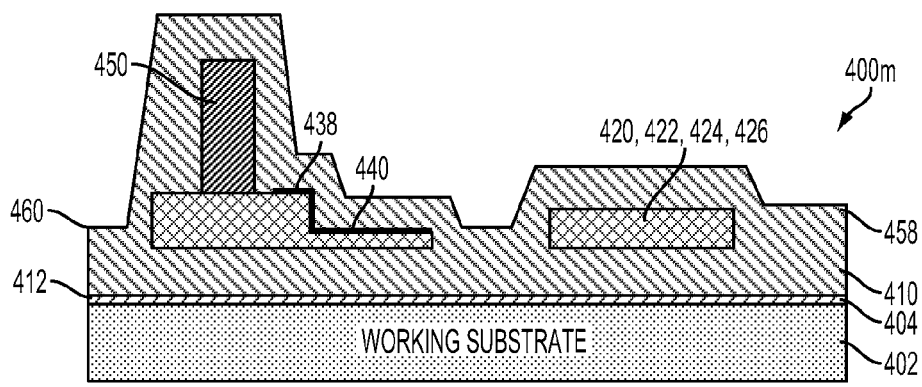
Figure 4N:
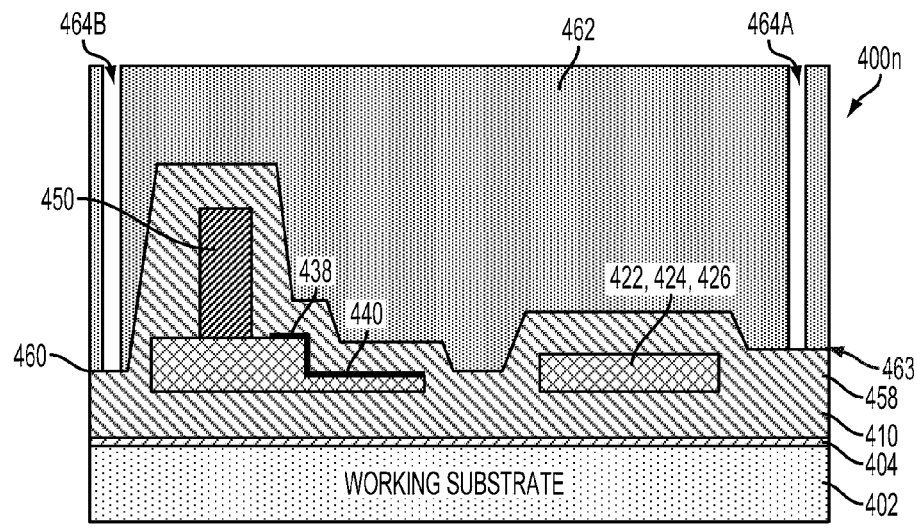
Figure 4O:
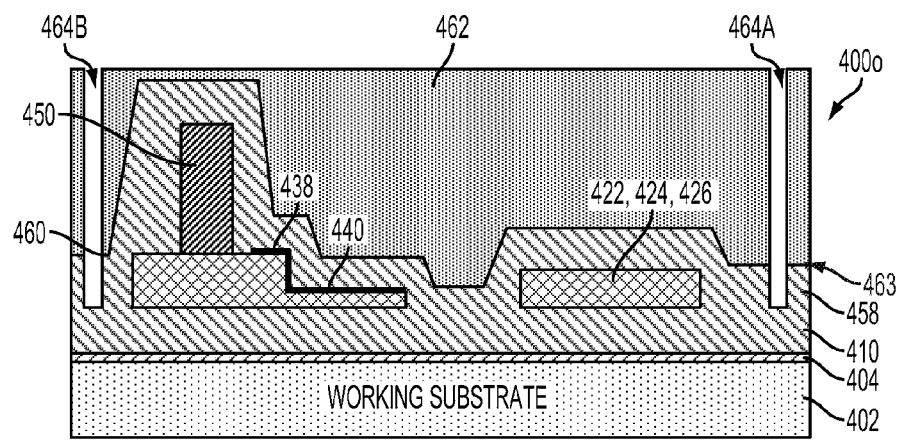
Figure 4P:
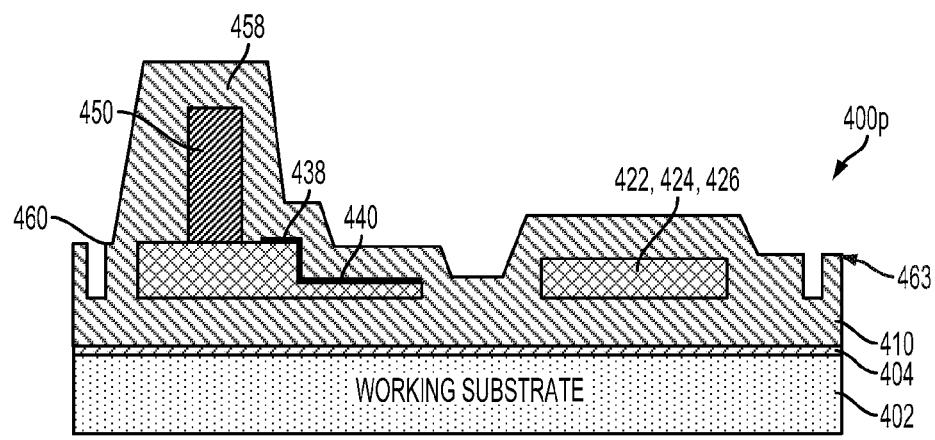
Figure 4Q:
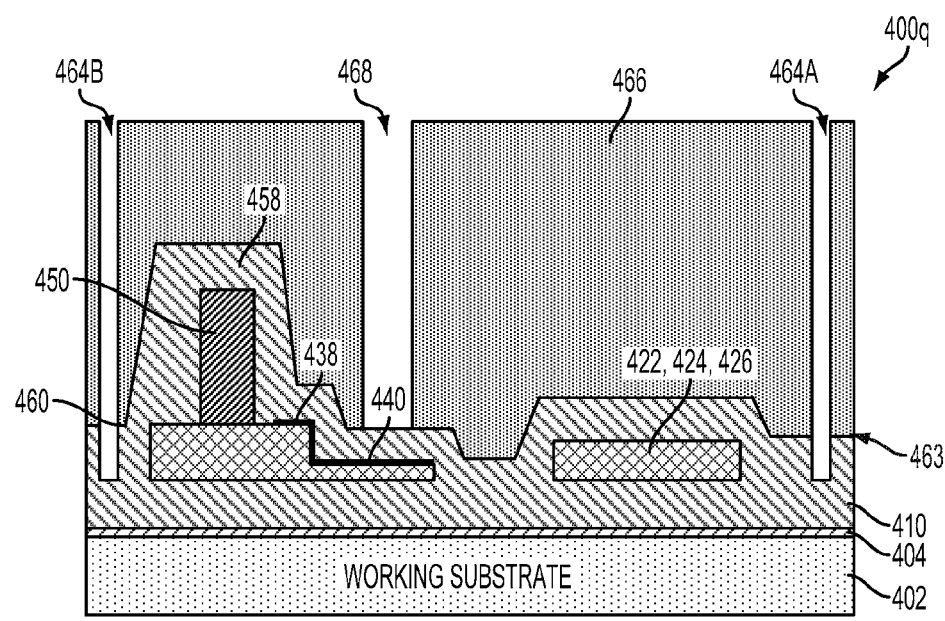
Figure 4R:
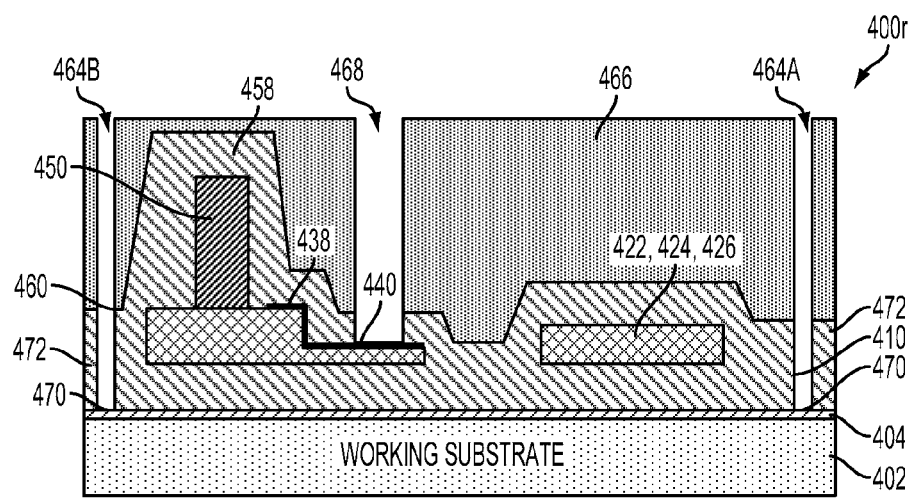
Figure 4S:
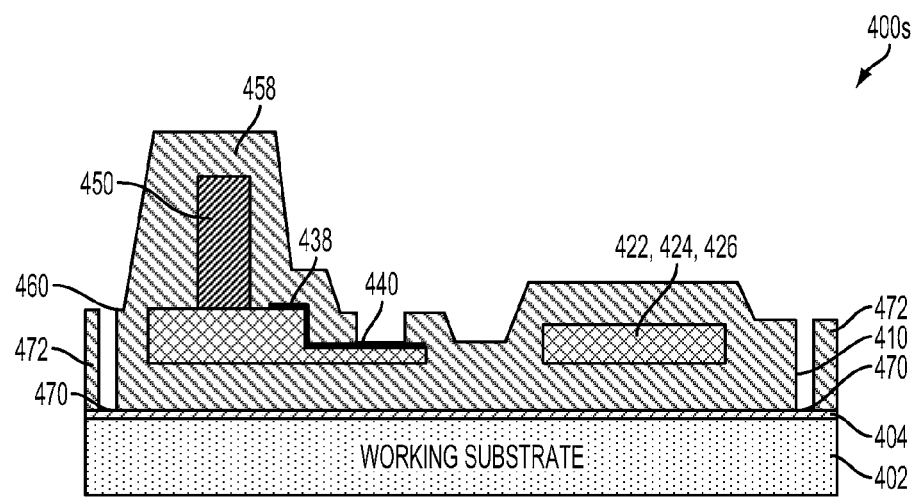
Figure 4T:
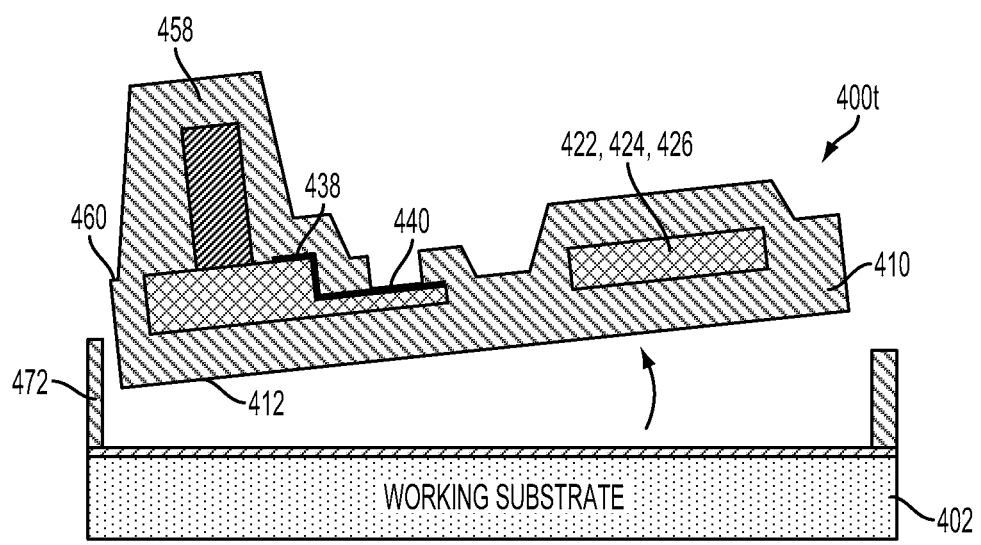

FIGS. 4A-4T illustrates stages of fabricating a bio-compatible device, in accordance with an example embodiment, to illustrate the method 300. The illustrations shown in FIGS. 4A-4T are generally shown in cross-sectional views to illustrate sequentially formed layers developed to create the bio-compatible device. The layers can be developed by microfabrication and/or manufacturing techniques such as, for example, electroplating, photolithography, deposition, and/or evaporation fabrication processes and the like. The various materials may be formed according to patterns using photoresists and/or masks to pattern materials in particular arrangements, such as to form wires, electrodes, electrical contacts, etc. Additionally, electroplating techniques may also be employed to coat an arrangement of electrodes with a metallic plating. For example, an arrangement of conductive material formed by a deposition and/or photolithography process can be plated with a metallic material to create a conductive structure with a desired thickness. However, the dimensions, including relative thicknesses and widths, of the various layers illustrated and described in connection with FIGS. 4A-4T to create a bio-compatible device are not illustrated to scale. Instead, the drawings in FIGS. 4A-4T schematically illustrate the ordering of the various layers for purposes of explanation only.

At block 302, the method 300 includes forming a first bio-compatible layer, where the first bio-compatible layer defines a first side of a bio-compatible device. FIG. 4A illustrates a working substrate 402 with a sacrificial layer 404 formed on the working substrate 402 to provide a partially-fabricated device 400a. The sacrificial layer 404 may have a surface 408.

In some examples, the sacrificial layer 404 may adhere to the working substrate 402. Moreover, in some examples, a bio-compatible layer formed on the sacrificial layer 404 may adhere to the sacrificial layer 404.

Moreover, the working substrate 402 may be cleaned before forming the sacrificial layer 404. The working substrate 402 may be cleaned in a variety of ways. For example, the working substrate 402 may be cleaned by soaking in a first fluid, rinsing with a second fluid, and drying with a gas. In some examples, the first fluid may include a solvent, such as acetone. Moreover, in some examples, the second fluid may include isopropyl alcohol (IPA). Further, in some examples, the gas may include nitrogen. All of the rinsing described herein may be performed in a variety ways, such as soaking in a bath in a tank, an automated spray, manually via a squirt bottle, etc.

Further, the working substrate 402 may be baked before forming the sacrificial layer 404. The working substrate 402 may be baked in a variety of ways. For example, the working substrate 402 may be baked at a temperature for a time period. In some examples, the temperature may be 90 degrees Celsius (C). Moreover, in some examples, the time period may be 2 minutes.

Further still, the working substrate 402 may be plasma cleaned before forming the sacrificial layer 404. The working substrate 402 may be plasma cleaned in a variety of ways. For example, the working substrate 402 may be plasma cleaned at a power for a time period. In some examples, the power may be high. Moreover, in some examples, the time period may be 5 minutes.

As shown in FIG. 4B, a first bio-compatible layer 410 is formed on the sacrificial layer 404 to provide a partially-fabricated device 400b. The first bio-compatible layer 410 may be formed on the sacrificial layer 404, such that the first bio-compatible layer 410 adheres to the sacrificial layer 404. The first bio-compatible layer 410 defines a first side 412 of a bio-compatible device. That is, the first bio-compatible layer 410 defines an outer edge of the bio-compatible device.

The first bio-compatible layer 410 may include a variety of materials. For example, the first bio-compatible layer 410 may include a polymeric material such as SCS parylene-C (e.g., dichlorodi-p-xylylene), a polyethylene terephthalate (PET), a polydimethysiloxane (PDMS), other silicone elastomers, and/or another bio-compatible polymeric material. The term "bio-compatibility," as used in this disclosure, refers generally to the ability of a material or device to co-exist with a biological host. Bio-compatible materials are generally those that do not bring about a host response (such as an immune response) that results in deleterious effects to either the biological host or the material. In addition to being bio-compatible, the first bio-compatible layer 410 may be an electrically insulating material to isolate encapsulated electronics from the surrounding environment (e.g., from current-carrying particles and/or fluids).

Moreover, the first bio-compatible layer 410 may have a variety of thicknesses. For example, the first bio-compatible layer 410 may have a thickness between 5 to 50 micrometers, such as 15 micrometers. Other thicknesses of the first bio-compatible layer 410 are possible as well.

In an example, the first bio-compatible layer 410 may be formed by a microfabrication process such as chemical vapor deposition, and provides a surface on which various components can be formed. The first bio-compatible layer 410 may be deposited onto the sacrificial layer 404 with a substantially uniform thickness such that a surface of the first bio-compatible layer 410 opposite the working substrate 402 forms a flat surface. In addition, the first bio-compatible layer 410 may have sufficient structural rigidity to be used as a substrate for assembling various components. In some examples, the first bio-compatible layer 410 may be a conformal coat.

In an example, equipment that forms the first bio-compatible layer 410 may be preheated for 1 hour before forming the first bio-compatible layer 410. Moreover, in an example, 35 grams of a polymeric material may be used to form the first bio-compatible layer 410.

Moreover, an adhesion promoter may be applied to a surface of the sacrificial layer 404 before the first bio-compatible layer 410 is formed. With such an arrangement, adhesion of the first bio-compatible layer 410 to the sacrificial layer 404 may be improved. For example, an adhesion promoter may be applied to the surface 408 of the sacrificial layer 404.

In some examples, the adhesion promoter may comprise 3-methacryloyloxypropyltrimethoxysilane. And in such examples, the adhesion promoter may be A174 sold by Specialty Coating Systems and/or Sigma Aldrich. Moreover, in some examples, the adhesion promoter may comprise hexamethyldisilazane (HDMS). Other adhesion promoters are possible as well.

The adhesion promoter may be applied in a variety of ways. For example, the adhesion promoter may be applied by spin coating at a rate, baking at a temperature for a first time period, rinsing with a fluid, and baking at the temperature for a second time period. In some examples, the rate may be 3000 rotations per minute (rpm). And in such examples, applying the adhesion promoter by spin coating may involve accelerating and/or decelerating the partially-fabricated device 400a at a rate between 100 to 3000 rpm per second, such as 1000 to 1500 rpm per second. Moreover, in some examples, the temperature may be 90 degrees C. Further, in some examples, the first time period may be 2 minutes. Further still, in some examples, the fluid may include IPA. And, in some examples, the second time period may be 1 minute.

In another example, the adhesion promoter may be applied by soaking the partially-fabricated device 400a in a mixture including the adhesion promoter for a first time period, air drying on a towel for a second time period, rinsing with one or more fluids, and drying with a gas. In some examples, the mixture may comprise 100 parts deionized water (DI water), 100 parts IPA, and 1 part the adhesion promoter. Moreover, in some examples, the mixture may settle for 2 hours before soaking the partially-fabricated device 400a in the mixture. Further, in some examples, the first time period may be 30 minutes. Moreover, in some examples, the second time period may be 30 minutes. Further, in some examples, the one or more fluids may include IPA and DI water. And, in some examples, the gas may include nitrogen. In such an example, soaking the partially-fabricated device 400a in a mixture including the adhesion promoter for the first time period, air drying on a towel for the second time period, rinsing with one or more fluids, and/or drying with the gas may occur at room temperature. Moreover, in such an example, applying the adhesion promoter may further involve baking the partially-fabricated device 400a at a temperature for a time period. In some examples, the temperature may be 90 degrees C. Moreover, in some examples, the time period may be 2 minutes.

Moreover, the partially-fabricated device 400a may be cleaned before applying the adhesion promoter to a surface of the sacrificial layer 404. The partially-fabricated device 400a may be cleaned in a variety of ways. For example, the partially-fabricated device 400a may be cleaned by rinsing in a fluid, drying with a gas, and baking at a temperature for a time period. In some examples, the fluid may include IPA. Moreover, in some examples, the gas may include nitrogen. Further, in some examples, the temperature may be 90 degrees C. Further still, in some examples, the time period may be 2 minutes.

Further, the partially-fabricated device 400a may be plasma cleaned before applying the adhesion promoter to a surface of the sacrificial layer 404. The partially-fabricated device 400a may be plasma cleaned in a variety of ways. For example, the partially-fabricated device 400a may be plasma cleaned at a power for a time period. In some examples, the power may be high. Moreover, in some examples, the time period may be 5 minutes.

Moreover, a surface of the sacrificial layer 404 may be treated, such that the first bio-compatible layer 410 bonds to the treated surface during formation of the first bio-compatible layer 410. For example, the surface 408 of the sacrificial layer 404 may be treated, such that the first bio-compatible layer 410 bonds to the treated surface during formation of the first bio-compatible layer 410. With this arrangement, the surface 408 may be roughened, such that adhesion of the first bio-compatible layer 410 to the sacrificial layer 404 may be improved.

The surface 408 may be treated in a variety of ways. For example, the surface 408 of the sacrificial layer 404 may be treated by etching using an inductively coupled plasma at a power for a time. In some examples, the inductively coupled plasma may include an oxygen plasma. Moreover, in some examples, the power may be 400 Watts (W) with a 300 W bias. Further, in some examples, the time period may be 1 to 3 minutes. In some examples, the inductively coupled plasma may unevenly etch the surface 408, such that the surface 408 may be roughened. Other plasmas and/or types of plasmas may be used as well, such as plasma asher, a reactive ion etcher, etc.

Referring back to FIG. 3, at block 304, the method 300 includes forming a first conductive layer over a portion of the first bio-compatible layer. As shown in FIG. 4C, a seed layer 414 is formed over the first bio-compatible layer 410 to provide a partially-fabricated device 400c. Such a seed layer 414 can be used to adhere to both the first bio-compatible layer 410, and any additional metal structure that is patterned over the seed layer 414, as will be described below. For example, the seed layer 414 may include one or more materials that both adheres well to the first bio-compatible layer 410 and serves as a guide to electroplate the remainder of a metal structure that forms a component. In such an example, the seed layer 414 may include palladium, titanium, and/or gold. In some examples, the seed layer 414 may include a palladium layer and a gold layer. In some examples, the seed layer 414 may include a titanium layer and a gold layer.

Moreover, the seed layer 414 may have a variety of thicknesses. For example, a palladium layer of the seed layer 414 may have a thickness between 20 to 30 nanometers, such as 30 nanometers. Moreover, a titanium layer of the seed layer 414 may have a thickness between 20 to 30 nanometers, such as 30 nanometers. Further, a gold layer of the seed layer 414 may have a thickness of 100 nanometers. Other thicknesses of the seed layer 414 are possible as well.

In an example, the seed layer 414 may be formed by a microfabrication process such as evaporation. However, in other examples, the seed layer 414 may be formed by other microfabrication processes, such as sputtering. In some examples, a palladium layer of the seed layer 414 may be formed over the first bio-compatible layer 410, and a gold layer of the seed layer 414 may be formed over the palladium layer of the seed layer 414. In some examples, a titanium layer of the seed layer 414 may be formed over the first bio-compatible layer 410, and a gold layer of the seed layer 414 may be formed over the titanium layer of the seed layer 414.

Moreover, the partially-fabricated device 400b may be cleaned before forming the seed layer 414 over the first bio-compatible layer 410. The partially-fabricated device 400b may be cleaned in a variety of ways. For example, the partially-fabricated device 400b may be cleaned by soaking in a first fluid, rinsing in a second fluid, and drying with a gas. In some examples, the first fluid may include a solvent, such as acetone. Moreover, in some examples, the second fluid may include IPA. Further, in some examples, the gas may include nitrogen.

Further, the partially-fabricated device 400b may be baked before forming the seed layer 414 over the first bio-compatible layer 410. The partially-fabricated device 400b may be baked at a temperature for a time period. In some examples, the temperature may be 90 degrees C. Moreover, in some examples, the time period may be 5 minutes. Further, in some examples, the partially-fabricated device 400b may be baked on a hot plate. After the partially-fabricated device 400b is baked, the partially-fabricated device 400b may be cooled to room temperature.

Further still, the partially-fabricated device 400b may be plasma cleaned before forming the seed layer 414 over the first bio-compatible layer 410. With this arrangement, a surface 411 of the first bio-compatible layer 410 (as shown in FIG. 4B) may be roughened, such that adhesion of the seed layer 414 to the first bio-compatible layer 410 may be improved.

The partially-fabricated device 400b may be plasma cleaned in a variety of ways. For example, the partially-fabricated device 400b may be plasma cleaned at a power for a time period. In some examples, the power may be high. Moreover, in some examples, the time period may be 5 minutes.

In another example, the surface 411 of the first bio-compatible layer may be treated before forming the seed layer 414. With this arrangement, the surface 411 of the first bio-compatible layer 410 may be roughened, such that adhesion of the seed layer 414 to the first bio-compatible layer 410 may be improved. The surface 411 may be treated in a variety of ways. For example, the surface 411 of the first bio-compatible layer 410 may be treated by etching using an inductively coupled plasma at a power for a time. In some examples, the inductively coupled plasma may include an oxygen plasma. Moreover, in some examples, the power may be 400 W with a 300 W bias. In some examples, the inductively coupled plasma may unevenly etch the surface 411, such that the surface 411 may be roughened. Further, in some examples, the time period may be 1 to 3 minutes. Other plasmas and/or types of plasmas may be used as well, such as plasma asher, a reactive ion etcher, etc.

As shown in FIG. 4D, a first mask 416 is formed over a portion 418 of the seed layer 414 to provide a partially-fabricated device 400d. The first mask 416 may include a variety of materials. For example, the first mask 416 may include a photoresist layer, such as a photoresist layer comprising 2-ethoxyethyl acetate. In such an example, the first mask 416 may be AZ4620® sold by Capital Scientific.

Moreover, the first mask 416 may have a variety of thicknesses. For example, the first mask 416 may have thicknesses of 5 micrometers. Other thicknesses of the first mask 416 are possible as well.

In an example, the first mask 416 may be formed over the portion 418 of the first bio-compatible layer 410 by spin coating and patterning. The first mask 416 may be spin coated in a variety of ways. For example, a material may be spin coated by placing the material on the partially-fabricated device 400c, applying a spread cycle, applying a spin cycle, and applying a deceleration cycle.

In some examples, placing the material on the partially-fabricated device 400c may include pouring (or pipetting) the material onto the partially-fabricated device 400c. Moreover, in some examples, applying the spread cycle may include rotating the partially-fabricated device 400c at a first rate for a first time period. And in such examples, the first rate may be 500 rpm. And in such examples, the first time period may be 8 seconds. With this arrangement, the material may be spread over the seed layer 414. The spread cycle may further include accelerating the partially-fabricated device 400c at a second rate for a second time period before rotating the partially-fabricated device 400c at the first rate for the first time period. In some examples, the second rate may be 250 rpm per second. Moreover, in some examples, the second time period may be 2 seconds.

Further, in some examples, applying the spin cycle may include rotating the partially-fabricated device 400c at a first rate for a first time period. And in such examples, the first rate may be 3000 rpm. And in such examples, the first time period may be 28 to 38 seconds. With this arrangement, the thickness of the first mask 416 may be formed. The spin cycle may further include accelerating the partially-fabricated device 400c at a second rate for a second time period before rotating the partially-fabricated device 400c at the first rate for the first time period. In some examples, the second rate may be 1500 rpm per second. Moreover, in some examples, the second time period may be 2 seconds.

Further still, in some examples, applying the deceleration cycle comprises decelerating the partially-fabricated device 400c at a rate for a time period. And in such examples, the rate may be 1500 rpm per second. And in such examples, the time period may be 2 seconds.

Moreover, in some examples, the partially-fabricated device 400c may be placed in a vacuum chuck before placing the material on the partially-fabricated device 400c. And in such examples, the partially-fabricated device 400c may be removed from the vacuum chuck after applying the declaration cycle.

After the first mask 416 is spin coated, the first mask 416 may be baked before patterning. The first mask 416 may be baked in a variety of ways. For example, the first mask 416 may be baked at a temperature for a time period. In some examples, the temperature may be 90 degrees C. Moreover, in some examples, the time period may be 2 minutes. After the first mask 416 is baked, the first mask 416 may be cooled to room temperature.

In addition, the first mask 416 may be patterned in a variety of ways. For example, a material may be patterned by exposing and developing. In such an example, the material may be exposed to light at an intensity for a first time period, and developed by soaking in a fluid for a second time period. In some examples, the light may be ultra violet light (UV light) that is generated by a mercury lamp. Moreover, in some examples, the intensity may be 16 to 19 milliwatts per centimeter (mW/cm$^2$). Further, in some examples, the first time period may be 10 to 12 seconds. Moreover, in some examples, the fluid may comprise four parts DI water and one part a fluid comprising potassium borates. And in such examples, the fluid comprising potassium borates may be AZ® 400K Developer sold by AZ Electronics Materials. Further still, in some examples, the second time period may be about 1 minute.

Moreover, the partially-fabricated device 400d may be further processed after formation of the first mask 416 over the portion 418 of the seed layer 414. The partially-fabricated device 400d may be further processed in a variety of ways. For example, the partially-fabricated device 400d may be further processed by rinsing in a fluid, blow drying with a gas, and baking at a temperature for a time period. In some examples, the fluid may include DI water. Moreover, in some examples, the gas may include nitrogen. Further, in some examples, the temperature may be 90 degrees C. Further still, in some examples, the time period may be 30 minutes. After the first mask 416 is further processed after formation of the first mask 416 over the portion 418 of the seed layer 414, the first mask 416 may be cooled to room temperature.

Further, the partially-fabricated device 400c may be cleaned before forming the first mask 416 over the portion 418 of the seed layer 414. The partially-fabricated device 400c may be cleaned in a variety of ways. For example, the partially-fabricated device 400c may be cleaned by soaking in a first fluid, rinsing in a second fluid, and drying with a gas. In some examples, the first fluid may include a solvent, such as acetone. Moreover, in some examples, the second fluid may include IPA. Further, in some examples, the gas may include nitrogen.

Further still, the partially-fabricated device 400c may be baked before forming the first mask 416 over the portion 418 of the seed layer 414. The partially-fabricated device 400c may be baked at a temperature for a time period. In some examples, the temperature may be 90 degrees C. Moreover, in some examples, the time period may be 2 minutes. Further, in some examples, the partially-fabricated device 400c may be baked on a hot plate. After the partially-fabricated device 400c is baked, the partially-fabricated device 400c may be cooled to room temperature.

As shown in FIG. 4E, a first conductive (e.g., metal) layer 420 is formed over exposed portions 428 of the seed layer 414 (i.e., the portions that are not covered by the first mask 416) to provide a partially-fabricated device 400e. The first conductive layer 420 may define components including an antenna 422, electrical contacts 424, and electrical interconnects 426.

The first conductive layer 420 may include a variety of conductive materials. For example, the first conductive layer 420 may include one or more layers of platinum, silver, gold, palladium, titanium, copper, chromium, nickel, aluminum, other metals or conductive materials, and combinations thereof. In some examples, the first conductive layer 420 may include a substantially transparent conductive material for at least some components (e.g., a material such as indium tin oxide). In an example, the first conductive layer 420 may comprise one layer of gold.

Moreover, the first conductive layer 420 may have a variety of thicknesses. For example, the first conductive layer 420 may have a thickness between 6 to 10 micrometers, such as between 6 to 7 micrometers, 7 to 8 micrometers, or 9 to 10 micrometers. Other thicknesses of the first conductive layer 420 are possible as well.

In an example, the first conductive layer 420 may be formed by a microfabrication process such as electroplating. Other microfabrication processes for forming the first conductive layer 420 are possible as well. The first conductive layer 420 may be electroplated in a variety ways. For example, the first conductive layer 420 may be electroplated in a bath at a current for a time period. In some examples, the current is 60 milliamps (mA). Moreover, in some examples, the time period is 60 to 75 minutes.

Moreover, the partially-fabricated device 400d may be plasma cleaned before forming the first conductive layer 420 over the exposed portions 428 of the seed layer 414. The partially-fabricated device 400d may be plasma cleaned in a variety of ways. For example, the partially-fabricated device 400d may be plasma cleaned at a power for a time period. In some examples, the power may be high. Moreover, in some examples, the time period may be 5 minutes.

The first mask 416 may then be removed and a second mask 429 is formed over the first conductive layer 420 to provide a partially-fabricated device 400f, as shown in FIG. 4F. The first mask 416 may be removed in a variety of ways. For example, the first mask 416 may be removed by soaking in a first fluid for a time period, rinsing in a second fluid, and drying with a gas. In some examples, the first fluid may include a solvent, such as acetone. Moreover, in some examples, the time period may be 2 minutes. Further, in some examples, the second fluid may include IPA. Further still, in some examples, the gas may include nitrogen. And, in an example, removal may further involve agitation during soaking in the first fluid. As another example, the first mask 416 may be removed using an inductively coupled plasma, such as oxygen plasma.

The second mask 429 may include a variety of materials. For example, the second mask 429 may include one or more photoresist layers, such as one photoresist layer comprising 2-ethoxyethyl acetate. In such an example, the second mask 429 may be AZ4620® sold by Capital Scientific. In another example, the second mask 429 may include one photoresist layer comprising 1-methoxy-2-propanol acetate. In such an example, the second mask 429 may be AZ nLOF 2070® sold by AZ Electronic Materials. In yet another example, the second mask 429 may include one photoresist layer comprising cyclohexanone. In such an example, the second mask 429 may be NR9-3000PY sold by Futurrex, Inc.

Moreover, the second mask 429 may have a variety of thicknesses. For example, the second mask 429 may have a thickness of 5 micrometers. Other thicknesses of the second mask 429 are possible as well.

In an example, the second mask 429 may be formed over the first conductive layer 420 by spin coating and patterning. The second mask 429 may be spin coated in a variety of ways. For example, a material may be spin coated by placing the material on the partially-fabricated device 400e (after the first mask 416 has been removed), applying a spread cycle, applying a spin cycle, and applying a deceleration cycle.

In some examples, placing the material on the partially-fabricated device 400e may include pouring (or pipetting) the material onto the partially-fabricated device 400e.

Moreover, in some examples, applying the spread cycle may include rotating the partially-fabricated device 400e at a first rate for a first time period. And in such examples, the first rate may be 500 rpm. And in such examples, the first time period may be 8 seconds. With this arrangement, the material may be spread over the partially-fabricated device 400e. The spread cycle may further include accelerating the partially-fabricated device 400e at a second rate for a second time period before rotating the partially-fabricated device 400e at the first rate for the first time period. In some examples, the second rate may be 250 rpm. Moreover, in some examples, the second time period may be 2 seconds.

Further, in some examples, applying the spin cycle may include rotating the partially-fabricated device 400e at a first rate for a first time period. And in such examples, the first rate may be 3000 rpm. And in such examples, the first time period may be 28 to 38 seconds. With this arrangement, the thickness of the second mask 429 may be formed. The spin cycle may further include accelerating the partially-fabricated device 400e at a second rate for a second time period before rotating the partially-fabricated device 400e at the first rate for the first time period. In some examples, the second rate may be 1500 rpm per second. Moreover, in some examples, the second time period may be 2 seconds.

Further still, in some examples, applying the deceleration cycle comprises decelerating the partially-fabricated device 400e at a rate for a time period. And in such examples, the rate may be 1500 rpm per second. And in such examples, the time period may be 2 seconds.

Moreover, in some examples, the partially-fabricated device 400e may be placed in a vacuum chuck before placing the material on the partially-fabricated device 400e. And in such examples, the partially-fabricated device 400e may be removed from the vacuum chuck after applying the deceleration cycle.

After the second mask 429 is spin coated, the second mask 429 may be baked before patterning. The second mask 429 may be baked in a variety of ways. For example, the second mask 429 may be baked at a temperature for a time period. In some examples, the temperature may be 90 degrees C. Moreover, in some examples, the time period may be 2 minutes. After the second mask 429 is baked, the second mask 329 may be cooled to room temperature.

In addition, the second mask 429 may be patterned in a variety of ways. For example, the material may be patterned by exposing and developing. In such an example, the material may be exposed to light at an intensity for a first time period, and developed by soaking in a fluid for a second time period. In some examples, the light may be ultra violet light (UV light) that is generated by a mercury lamp. Moreover, in some examples, the intensity may be 16 to 19 mW/cm$^2$. Further, in some examples, the first time period may be 10 to 12 seconds. Moreover, in some examples, the fluid may comprise four parts DI and one part a fluid comprising potassium borates. And in such examples, the fluid comprising potassium borates may be AZ® 400K Developer sold by AZ Electronics Materials. Further still, in some examples, the second time period may be about 1 minute.

Moreover, the partially-fabricated device 400f may be further processed after formation of the second mask 429 over the first conductive layer 420. The partially-fabricated device 400f may be further processed in a variety of ways. For example, the partially-fabricated device 400f may be further processed by rinsing in a fluid, blow drying with a gas, and baking at a temperature for a time period. In some examples, the fluid may include DI water. Moreover, in some examples, the gas may include nitrogen. Further, in some examples, the temperature may be 90 degrees C. Further still, in some examples, the time period may be 30 minutes. After the second mask 429 is processed after formation, the second mask 429 may be cooled to room temperature.

Further, the partially-fabricated device 400e (after the first mask 416 has been removed) may be cleaned before forming the second mask 429 over the first conductive layer 420. The partially-fabricated device 400e may be cleaned in a variety of ways. For example, the partially-fabricated device 400e may be cleaned by soaking in a first fluid, rinsing in a second fluid, and drying with a gas. In some examples, the first fluid may include a solvent, such as acetone. Moreover, in some examples, the second fluid may include IPA. Further, in some examples, the gas may include nitrogen.

Further still, the partially-fabricated device 400e (after the first mask 416 has been removed) may be baked before forming the second mask 429 over the first conductive layer 420. The partially-fabricated device 400e may be baked at a temperature for a time period. In some examples, the temperature may be 90 degrees C. Moreover, in some examples, the time period may be 2 minutes. Further, in some examples, the partially-fabricated device 400e may be baked on a hot plate. After the partially-fabricated device 400e is baked, the partially-fabricated device 400e may be cooled to room temperature.

As shown in FIG. 4G, the portion 418 of the seed layer 414 is removed and the second mask 429 is removed to provide a partially-fabricated device 400g. In some examples, a gold layer of the portion 418 of the seed layer 414 and/or a palladium layer of the portion 418 of the seed layer 414 may be removed.

The portion 418 of the seed layer 414 may be removed in a variety of ways. For example, the portion 418 of the seed layer 414 may be removed by wet etching. The gold layer of the portion 418 of the seed layer 414 may be wet etched in a variety of ways. For example, the gold layer of the portion 418 of the seed layer 414 may be wet etched for a time period at a temperature. In some examples, the time period may be between 1 to 2 minutes. Moreover, in some examples, the temperature may be room temperature. And, in some examples, removing the gold layer of the portion 418 of the seed layer 414 may involve agitation (e.g., constant agitation) during wet etching. After the gold layer of the portion 418 of the seed layer 414 is wet etched, removing the gold layer of the portion 418 of the seed layer 414 may involve rinsing in a fluid and drying with a gas. In some examples, the fluid may include DI water. Moreover, in some examples, the gas may include nitrogen.

Moreover, the palladium layer of the portion 418 of the seed layer 414 may be wet etched in a variety of ways. For example, the palladium layer of the portion 418 of the seed layer 414 may be wet etched for a time period at a temperature. In some examples, the time period may be 30 seconds. Moreover, in some examples, the temperature may be 70 degrees C. After the palladium layer of the portion 418 of the seed layer 414 is wet etched, removing the palladium layer of the portion 418 of the seed layer 414 may involve rinsing in a fluid and drying with a gas. In some examples, the fluid may include DI water. Moreover, in some examples, the gas may include nitrogen.

The second mask 429 may be removed in a variety of ways. For example, the second mask 429 may be removed by soaking in a first fluid for a time period, rinsing in a second fluid, and drying with a gas. In some examples, the first fluid may include a solvent, such as acetone. Moreover, in some examples, the time period may be 2 minutes. Further, in some examples, the second fluid may include IPA. Further still, in some examples, the gas may include nitrogen. And, in an example, removal may further involve agitation during soaking in the first fluid. As another example, the second mask 429 may be removed using an inductively coupled plasma, such as an oxygen plasma.

The process illustrated by FIGS. 4D-4G can then be repeated to add more thickness to the first conductive layer 420. For example, referring to FIG. 4H, another mask layer can be formed over a portion of the first bio-compatible layer 410 and over a portion 420B of the first conductive layer 420 leaving a portion 420A of the first conductive layer 420 exposed. Another conductive layer can be formed over the exposed portion 420A so as to increase the thickness of the first conductive layer 420 at the portion 420A. The other mask layer may then be removed to result in partially-fabricated device 400h shown in FIG. 4H. Thus, the first conductive layer 420, in some examples, may have a non-uniform thickness.

Referring back to FIG. 3, at block 306, the method 300 includes forming a second conductive layer over a portion of the first conductive layer. As shown in FIG. 4I, a third mask 430 is formed over a portion 432 of the first bio-compatible layer 410 and a portion 434 the first conductive layer 420 to provide a partially-fabricated device 400i. The third mask 430 may include a variety of materials. For example, the third mask 430 may include one or more photoresist layers, such as one photoresist layer comprising 2-ethoxyethyl acetate. In such an example, the third mask 430 may be AZ4620® sold by Capital Scientific. In another example, the third mask 430 may include one photoresist layer comprising 1-methoxy-2-propanol acetate. In such an example, the third mask 430 may be AZ nLOF 2070® sold by AZ Electronic Materials. In yet another example, the third mask 430 may include one photoresist layer comprising cyclohexanone. In such an example, the third mask 430 may be NR9-3000PY sold by Futurrex, Inc.

Moreover, the third mask 430 may have a variety of thicknesses. For example, the third mask 430 may have a thicknesses of 5 micrometers. Other thicknesses of the third mask 430 are possible as well.

In an example, the third mask 430 may be formed over the portion 432 of the first bio-compatible layer 410 and the portion 434 of the first conductive layer 420 by spin coating and patterning. The third mask 430 may be spin coated in a variety of ways. For example, a material may be spin coated by placing the material on the partially-fabricated device 400*h*, applying a spread cycle, applying a spin cycle, and applying a deceleration cycle.

In some examples, placing the material on the partially-fabricated device 400*h* may include pouring (or pipetting) the material onto the partially-fabricated device 400*h*.

Moreover, in some examples, applying the spread cycle may include rotating the partially-fabricated device 400*h* at a first rate for a first time period. And in such examples, the first rate may be 500 rpm. And in such examples, the first time period may be 8 seconds. With this arrangement, the material may be spread over the partially-fabricated device 400*h*. The spread cycle may further include accelerating the partially-fabricated device 400*h* at a second rate for a second time period before rotating the partially-fabricated device 400*h* at the first rate for the first time period. In some examples, the second rate may be 250 rpm. Moreover, in some examples, the second time period may be 2 seconds.

Further, in some examples, applying the spin cycle may include rotating the partially-fabricated device 400*h* at a first rate for a first time period. And in such examples, the first rate may be 3000 rpm. And in such examples, the first time period may be 28 to 38 seconds. With this arrangement, the thickness of the third mask 430 may be formed. The spin cycle may further include accelerating the partially-fabricated device 400*h* at a second rate for a second time period before rotating the partially-fabricated device 400*h* at the first rate for the first time period. In some examples, the second rate may be 1500 rpm per second. Moreover, in some examples, the second time period may be 2 seconds.

Further still, in some examples, applying the deceleration cycle comprises decelerating the partially-fabricated device 400*h* at a rate for a time period. And in such examples, the rate may be 1500 rpm per second. And in such examples, the time period may be 2 seconds.

Moreover, in some examples, the partially-fabricated device 400*h* may be placed in a vacuum chuck before placing the material on the partially-fabricated device 400*h*. And in such examples, the partially-fabricated device 400*h* may be removed from the vacuum chuck after applying the deceleration cycle.

After the third mask 430 is spin coated, the third mask 430 may be baked before patterning. The third mask 430 may be baked in a variety of ways. For example, the third mask 430 may be baked at a temperature for a time period. In some examples, the temperature may be 90 degrees C. Moreover, in some examples, the time period may be 2 minutes. After the third mask 430 is baked, the third mask 430 may be cooled to room temperature.

In addition, the third mask 430 may be patterned in a variety of ways. For example, the material may be patterned by exposing and developing. In such an example, the material may be exposed to light at an intensity for a first time period, and developed by soaking in a fluid for a second time period. In some examples, the light may be ultra violet light (UV light) that is generated by a mercury lamp. Moreover, in some examples, the intensity may be the intensity may be 16 to 19 mW/cm$^2$. Further, in some examples, the first time period may be 10 to 12 seconds. Moreover, in some examples, the fluid may comprise four parts DI and one part a fluid comprising potassium borates. And in such examples, the fluid comprising potassium borates may be AZ® 400K Developer sold by AZ Electronics Materials. Further still, in some examples, the second time period may be about 1 minute.

Moreover, the partially-fabricated device 400*i* may be further processed after formation of the third mask 430 over the portion 432 of the first bio-compatible layer 410 and the portion 434 the first conductive layer 420. The partially-fabricated device 400*i* may be further processed in a variety of ways. For example, the partially-fabricated device 400*i* may be further processed by rinsing in a fluid, blow drying with a gas, and baking at a temperature for a time period. In some examples, the fluid may include DI water. Moreover, in some examples, the gas may include nitrogen. Further, in some examples, the temperature may be 90 degrees C. Further still, in some examples, the time period may be 30 minutes. After the third mask 430 is processed after formation, the third mask 430 may be cooled to room temperature.

Further, the partially-fabricated device 400*h* may be cleaned before forming the third mask 430 over the portion 432 of the first bio-compatible layer 410 and the portion 434 of the first conductive layer 420. The partially-fabricated device 400*h* may be cleaned in a variety of ways. For example, the partially-fabricated device 400*h* may be cleaned by soaking in a first fluid, rinsing in a second fluid, and drying with a gas. In some examples, the first fluid may include a solvent, such as acetone. Moreover, in some examples, the second fluid may include IPA. Further, in some examples, the gas may include nitrogen.

Further still, the partially-fabricated device 400*h* may be baked before forming the third mask 430 over the portion 432 of the first bio-compatible layer 410 and the portion 434 of the first conductive layer 420. The partially-fabricated device 400*h* may be baked at a temperature for a time period. In some examples, the temperature may be 90 degrees C. Moreover, in some examples, the time period may be 2 minutes. Further, in some examples, the partially-fabricated device 400*h* may be baked on a hot plate. After the partially-fabricated device 400*h* is baked, the partially-fabricated device 400*h* may be cooled to room temperature.

As shown in FIG. 4*j*, a second conductive layer 436 is formed over exposed portions 444 of the first conductive layer 420 (i.e., the portions that are not covered by the third mask 430) to provide a partially-fabricated device 400*j*. In some examples, the second conductive layer 436 may also be formed over an exposed portion 446 of the first bio-compatible layer 410 as well (not shown). The second conductive layer 436 may, for example, define electrical interconnects 438 and sensor electrodes 440.

The second conductive layer 436 may include a variety of conductive materials. For example, the second conductive layer 436 may include one or more layers of platinum, silver, gold, palladium, titanium, copper, chromium, nickel, aluminum, other metals or conductive materials, and combinations thereof. In an example, the second conductive layer may comprise a titanium layer, a palladium layer, and a platinum layer.

Moreover, the second conductive layer 436 may have a variety of thicknesses. For example, a titanium layer of the second conductive layer 436 may have a thickness between 10 to 50 nanometers, such as 30 nanometers; a palladium layer of the second conductive layer 436 may have a thickness between 10 to 50 nanometers, such as 30 nanometers; and a platinum layer of the second conductive layer 436 may have a thickness between 50 to 300 nanometers, such as 100 or 120 nanometers. Other thicknesses of the second conductive layer 436 are possible as well.

In an example, the second conductive layer 436 may be formed by a microfabrication process such as sputtering. However, in other examples, the second conductive layer 436 may be formed by other microfabrication processes such as evaporation. In some examples, a titanium layer of the second conductive layer 436 may be formed over the exposed portions 444 of the first conductive layer 420, a palladium layer of the second conductive layer 436 may be formed over the titanium layer, and a platinum layer of the second conductive layer 436 may be formed over the palladium layer.

Moreover, the partially-fabricated device 400i may be plasma cleaned before forming the second conductive layer 436 over the exposed portions 444 of the first conductive layer 420. The partially-fabricated device 400i may be plasma cleaned in a variety of ways. For example, the partially-fabricated device 400i may be plasma cleaned at a power for a time period. In some examples, the power may be high. Moreover, in some examples, the time period may be 60 seconds.

The third mask 430 may then be removed to provide a partially-fabricated device 400k, as shown in FIG. 4K. The third mask 430 may be removed in a variety of ways. For example, the third mask 430 may be removed by soaking in a first fluid for a first time period, rinsing in a second fluid, drying with a gas, and baking at a temperature for a second time period. In some examples, the first fluid may include a solvent, such as acetone. Moreover, in some examples, the first time period may be 1 to 5 hours, such as 1 to 2 hours or 4 to 5 hours. Further, in some examples, the second fluid may include IPA. Further still, in some examples, the gas may include nitrogen. Moreover, in some examples, the temperature may be 90 degrees C. Further, in some examples, the second time period may be 5 minutes. And, in an example, removal may further involve sonication for a time period (e.g., 2 to 3 seconds) after soaking in the first fluid. For instance, in some examples, removal may involve sonication for the time period after soaking in the first fluid for 1 hour. As another example, the third mask 430 may be removed using an inductively coupled plasma, such as an oxygen plasma.

After the third mask 430 is removed, the partially-fabricated device 400k may be rinsed in a fluid, dried with a gas, and baked at a temperature for a time period. In some examples, the fluid may include IPA. Moreover, in some examples, the gas may include nitrogen. Further, in some examples, the temperature may be 90 degrees C. Further still, in some examples, the time period may be 5 minutes.

Together, the first conductive layer 420 and the second conductive layer 436 form a conductive pattern 448. The conductive pattern 448 defines the antenna 422, the electrical contacts 424, the electrical interconnects 426, the electrical interconnects 438, and the sensor electrodes 440.

Referring back to FIG. 3, at block 308, the method 300 includes mounting an electronic component to a portion of the first conductive layer not covered by the second conductive layer. As shown in FIG. 4L, an electronic component 450 is mounted to a portion of the first conductive layer 420 not covered by the second conductive layer 436 to provide a partially-fabricated device 400l, as shown in FIG. 4L. The electronic component 450 could include, for example, one or more integrated circuits (ICs) and/or one or more discrete electronic components. Heat, pressure, a pick-and-place tool and a bonding medium (anisotropic conductive paste (ACP), anisotropic conductive film (ACF), solder and flux, solder paste, solder followed by underfill, etc.), or a flip-chip bonder, for example, may be used to adhere a first surface 452 of the electronic component 450 to the first conductive layer 420. The electronic component 450 has a second surface 454 opposite the first surface 452.

Referring back to FIG. 3, at block 310, the method 300 includes forming a second bio-compatible layer over the first bio-compatible layer, the electronic component, the first conductive layer and the second conductive layer, where the second bio-compatible layer defines a second side of the bio-compatible device. As shown in FIG. 4L, a surface 456 of the first bio-compatible layer 410 may be treated such that a surface of another bio-compatible layer bonds to the surface during formation of the other bio-compatible layer. The surface 456 of the first bio-compatible layer 410 may be treated in a variety of ways. For example, the surface 456 of the first bio-compatible layer 410 may be treated by etching using an inductively coupled plasma at a power for a time period. With this arrangement, the surface 456 of the first bio-compatible layer 410 may be roughened. In some examples, the inductively coupled plasma may include an oxygen plasma. Moreover, in some examples, the power may be 400 W with a 300 W bias. Further, in some examples, the time period may be 1 minute. In some examples, the inductively coupled plasma may unevenly etch the surface 456, such that the surface 456 may be roughened. Other plasmas and/or types of plasmas may be used as well, such as a plasma asher, a reactive ion etcher, etc.

The partially-fabricated device 400l may be baked at a temperature for a time period before treating the surface 456 of the first bio-compatible layer 410. In some examples, the temperature may be 90 degrees C. Moreover, in some examples, the time period may be 1 hour.

As shown in FIG. 4M, a second bio-compatible layer 458 is formed over the first bio-compatible layer 410, the electronic component 450, the antenna 422, the electrical interconnects 438, the electrical contacts 424, and the electrical interconnects 426 to provide a partially-fabricated device 400m. The second bio-compatible layer 458 defines a second side 460 of the bio-compatible device. That is, the second bio-compatible layer 458 defines an outer edge of the bio-compatible device.

In an example, the second bio-compatible layer 458 can be composed of the same polymeric material as the first bio-compatible layer 410. However, in other examples, the second bio-compatible layer 458 can be composed of a different polymeric material than the first bio-compatible 410. The second bio-compatible layer 458 can be any one of the polymeric materials mentioned herein that is both bio-compatible and electrically insulating. The second bio-compatible layer 458 thus serves to seal and insulate the components.

Moreover, the second bio-compatible layer 458 may have a variety of thicknesses. For example, the second bio-compatible layer 458 may have a thickness between one or more embedded components and a surface of the second bio-compatible layer 458 between 5 to 100 micrometers, such as 15 micrometers. Other thicknesses for the second bio-compatible layer 458 are possible as well.

In an example, the second bio-compatible layer 458 may be formed the same or similar way as the first bio-compatible layer 410 may be formed. However, in other examples, the second bio-compatible layer 458 may be formed by a different process (or processes) than the process (or processes) used to form the first bio-compatible layer 410.

For example, the second bio-compatible layer 458 may be formed by a microfabrication process such as chemical vapor deposition. The deposition of the second bio-compatible layer 458 may result in a conformal coating over the assembled components. Moreover, in an example, 35 grams of a polymeric material may be used to form the second bio-compatible layer 458.

The second bio-compatible layer 458 may be deposited to create a continuous layer that spans the entirety of the assembled components. The second bio-compatible layer 458 can span a region that extends beyond a footprint of the assembled components. As a result, the assembled components can be surrounded by portions of the second bio-compatible layer 458 that rest directly on the first bio-compatible layer 410.

Additionally or alternatively, after the second bio-compatible layer 458 is formed over first bio-compatible layer 410, the electronic component 450, the antenna 422, the electrical interconnects 438, the electrical contacts 424, and the electrical interconnects 426, the first bio-compatible layer 410 and the second bio-compatible layer 458 may be annealed and/or sintered. With this arrangement, the second bio-compatible layer 458 may bond to the first bio-compatible layer 410.

Moreover, the partially-fabricated device 400*l* may be cleaned before forming the second bio-compatible layer 458 over the first bio-compatible layer 410, the electronic component 450, the antenna 422, the electrical interconnects 438, the electrical contacts 424, and the electrical interconnects 426. The partially-fabricated device 400*l* may be cleaned in a variety of ways. For example, the partially-fabricated device 400*l* may be cleaned by rinsing in a fluid, drying with a gas, and baking at a temperature for a time period. In some examples, the fluid may include DI water. Moreover, in some examples, the gas may include nitrogen. Further, in some examples, the temperature may be 90 degrees C. Further still, in some examples, the time period may be 60 minutes.

Further, the partially-fabricated device 400*l* may be plasma cleaned before forming the second bio-compatible layer 458 over the first bio-compatible layer 410, the electronic component 450, the antenna 422, the electrical interconnects 438, the electrical contacts 424, and the electrical interconnects 426. The partially-fabricated device 400*l* may be plasma cleaned in a variety of ways. For example, the partially-fabricated device 400*l* may be plasma cleaned at a power for a time period. In some examples, the power may be high. Moreover, in some examples, the time period may be 5 minutes.

Referring back to FIG. 3, at block 312, the method 300 includes forming a first etch mask to partially cover the second bio-compatible layer, thereby exposing a first portion of the second bio-compatible layer. As shown in FIG. 4N, a first etch mask 462 is formed over a portion 463 of the second bio-compatible layer 458 to provide a partially-fabricated device 400*n*. FIG. 4N shows the first etch mask 462 partially covers the second bio-compatible layer 458 thereby exposing portions 464A and 464B of the second bio-compatible layer 458.

The first etch mask 462 may include a variety of materials. For example, the first etch mask 462 may include one or more photoresist layers, such as one photoresist layer comprising cyclopentanone. In such an example, the first etch mask 462 may be KMPR® sold by Micro Chem. However, in other examples, the first etch mask 462 may include one or more metal layers and/or one or more nitride layers.

Moreover, the first etch mask 462 may have a variety of thicknesses. For example, the first etch mask 462 may have a thickness between 100 to 150 micrometers, such as 120, 130, or 150 micrometers. Other thicknesses of the first etch mask 462 are possible as well.

In an example, the first etch mask 462 may be formed by spin coating and patterning. However, in other examples, the etch mask 462 may be formed by microfabrication processes such as evaporation and/or sputtering.

The first etch mask 462 may be spin coated in a variety of ways. For example, the first etch mask 462 may be spin coated in steps. In such an example, a first step may involve placing a first material on the partially-fabricated device 400*m*, applying a spread cycle, applying a spin cycle, and applying a deceleration cycle.

In some examples, placing the first material on the partially-fabricated device 400*m* may include pouring (or pipetting) the first material onto the partially-fabricated device 400*m*. Moreover, in some examples, applying the spread cycle may include rotating the partially-fabricated device 400*m* at a first rate for a first time period. And in such examples, the first rate may be 500 rpm. And in such examples, the first time period may be 5 seconds. With this arrangement, the first material may be spread over the partially-fabricated device 400*m*. The spread cycle may further include accelerating the partially-fabricated device 400*m* at a second rate for a second time period before rotating the partially-fabricated device 400*m* at the first rate for the first time period. In some examples, the second rate may be 100 rpm per second. Moreover, in some examples, the second time period may be 5 seconds.

Further, in some examples, applying the spin cycle may include rotating the partially-fabricated device 400*n* at a first rate for a first time period. And in such examples, the first rate may be 1000 rpm. And in such examples, the first time period may be 38 to 118 seconds. With this arrangement, a first portion of the thickness of the first etch mask 462 may be formed. The spin cycle may further include accelerating the partially-fabricated device 400*m* at a second rate for a second time period before rotating the partially-fabricated device 400*m* at the first rate for the first time period. In some examples, the second rate may be 500 rpm per second. Moreover, in some examples, the second time period may be 2 seconds.

Further still, in some examples, applying the deceleration cycle comprises decelerating the partially-fabricated device 400*m* at a rate for a time period. And in such examples, the rate may be 500 rpm per second. And in such examples, the time period may be 2 seconds. Moreover, in some examples, the partially-fabricated device 400*m* may be placed in a vacuum chuck before placing the first material on the partially-fabricated device 400*m*.

The first step may further involve baking the first material at a temperature for a time period. In some examples, the temperature is 90 degrees C. Moreover, in some examples, the time period may be 5 minutes. In such an example, a second step may involve placing a second material on the first material, applying a spread cycle, applying a spin cycle, and applying a deceleration cycle.

In some examples, placing the second material on the first material may include pouring (or pipetting) the second material onto the first material.

Moreover, in some examples, applying the spread cycle may include rotating the partially-fabricated device 400*m* at a first rate for a first time period. And in such examples, the first rate may be 500 rpm. And in such examples, the first time period may be 5 seconds. With this arrangement, the second material may be spread over the first material. The spread cycle may further include accelerating the partially-fabricated device 400*m* at a second rate for a second time period before rotating the partially-fabricated device 400m at the first rate for the first time period. In some examples, the second rate may be 100 rpm per second. Moreover, in some examples, the second time period may be 5 seconds.

Further, in some examples, applying the spin cycle may include rotating the partially-fabricated device 400m at a first rate for a first time period. And in such examples, the first rate may be 1000 rpm. And in such examples, the first time period may be 38 to 118 seconds. With this arrangement, a second portion of the thickness of the first etch mask 462 may be formed. The spin cycle may further include accelerating the partially-fabricated device 400m at a second rate for a second time period before rotating the partially-fabricated device 400m at the first rate for the first time period. In some examples, the second rate may be 500 rpm per second. Moreover, in some examples, the second time period may be 2 seconds.

Further still, in some examples, applying deceleration cycle comprises decelerating the partially-fabricated device 400m at a rate for a time period. And in such examples, the rate may be 500 rpm per second. And in such examples, the time period may be 2 seconds.

And in some examples, the partially-fabricated device 400m may be removed from the vacuum chuck after applying the deceleration cycle.

After the first and second material is spin coated, the first and second material may be baked at a first temperature to a second temperature at a rate for a time period. In some examples, the first temperature is 65 degrees C. Moreover, in some examples, the second temperature is 90 to 95 degrees C. Further, in some examples, the rate is 120 degrees C. per hour. Further still, in some examples, the time period may be 1 hour. In another example, the first and second material may be baked at 90 degrees C. for 1 hour.

After the first and second material is baked, the first and second material may be cooled to room temperature at a rate. In some examples, the rate is 450 degrees C. per hour or 120 degrees C. per hour.

The first etch mask may 462 be patterned in a variety of ways. For example, the first and second material may be patterned by exposing and developing. And, in such an example, the first and second material may be exposed and developed in steps.

In such an example, a first step may involve exposing the first and second material to light at an intensity for a first time period. In some examples, the light may be ultra violet light (UV light) that may be generated by a mercury lamp. Moreover, in some examples, the intensity may be the intensity may be 16 to 19 mW/cm$^2$. Further, in some examples, the first time period may be 30 seconds. Moreover, in such an example, a second step may involve repeating the first step. In another example, the first time period may include one or more cycles (e.g., 3 cycles) where each of the one or more cycles includes an exposure time period (e.g., 20 seconds) and a waiting time period (e.g., 30 seconds to 2 minutes).

Further, in such an example, a third step may involve baking the first and second material at a temperature for a second time period. In some examples, the temperature may be 90 degrees C. Moreover, in some examples, the second time period may be 2 minutes. Further still, in such an example, a fourth step may involve developing the first and second material using a fluid comprising 1-methoxy-2-propyl acetate. In an example, the fluid may be SU-8 Developer® sold by Micro Chem. In some examples, the time period may be 15 or 10 minutes.

Moreover, the partially-fabricated device 400n may be further processed after formation of the first etch mask 462 over the portion 463 of the second bio-compatible layer 458. The partially-fabricated device 400n may be further processed in a variety of ways. For example, the partially-fabricated device 400n may be further processed by rinsing in a fluid, blow drying with a gas, and baking at a temperature for a time period. In some examples, the fluid may include IPA. Moreover, in some examples, the gas may include nitrogen. Further, in some examples, the temperature may be 90 degrees C. Further still, in some examples, the time period may be 60 minutes.

Moreover, the partially-fabricated device 400m may be cleaned before forming the first etch mask 462 over the portion 463 of the second bio-compatible layer 458. The partially-fabricated device 400m may be cleaned in a variety of ways. For example, the partially-fabricated device 400m may be cleaned by soaking in a first fluid, rinsing in a second fluid, and drying with a gas. In some examples, the first fluid may include a solvent, such as acetone. Moreover, in some examples, the second fluid may include IPA. Further, in some examples, the gas may include nitrogen.

Further, the partially-fabricated device 400m may be baked before forming the first etch mask 462 over the portion 463 of the second bio-compatible layer 458. The partially-fabricated device 400m may be baked in a variety of ways. For example, the partially-fabricated device 400m may be baked at a temperature for a time period. In some examples, the temperature may be 90 degrees C. Moreover, in some examples, the time period may be 5 minutes. Further, in some examples, the partially-fabricated device 400m may be baked on a hot plate. After the partially-fabricated device 400m is baked, the partially-fabricated device 400m may be cooled to room temperature.

Referring back to FIG. 3, at block 314, the method 300 includes removing the first portion of the second bio-compatible layer. As shown in FIG. 4O, exposed portions 464A and 464B of the second bio-compatible layer 458 (i.e., the portions that are not covered by the first etch mask 462) are removed to provide a partially-fabricated device 400o. In an example, the exposed portions 464A and 464B of the second bio-compatible layer 458 are removed by etching using an inductively coupled plasma at a power for a time period. In some examples, the inductively coupled plasma may include an oxygen plasma. Moreover, in some examples, the power may be 400 W at a 300 W bias. Further, in some examples, the time period may be 33 minutes. And, in such an example, the etching may comprise one or more cycles that comprises an etch period followed by a rest period, such that the partially-fabricated device 400o may cool down. In some examples, the etch period may be 3 minutes. Moreover, in some examples, the rest period may be 2 minutes. Further, in some examples, the one or more cycles may be 11 cycles. And, in some examples, the one or more cycles may be applied in sequence. Other plasmas and/or types of plasmas may be used as well, such as a plasma asher, a reactive ion etcher, etc.

In an example, the portions 464A and 464B of the second bio-compatible layer 458 (and possibly corresponding portions of the first-bio-compatible layer 410) are etched without exposing the sacrificial layer 404. The remaining portion of the first etch mask 462 may then be removed as shown in FIG. 4P to form partially-fabricated device 400p. The first etch mask may, for example, be removed by an inductively coupled plasma.

Referring back to FIG. 3, at block 316, the method 300 includes forming a second etch mask to partially cover the second bio-compatible layer, thereby exposing a second portion of the second bio-compatible layer, where the second portion of the second bio-compatible layer covers, at least partially, the second conductive layer. As shown in FIG. 4Q, a second etch mask 466 may be formed over portions of the second bio-compatible layer 458 exposing portions 464A, 464B, and 468 of the second bio-compatible layer 458 to form partially-fabricated device 400*q*. The exposed portion 468 of the second-bio compatible layer 458 covers, at least partially, the second conductive layer 436, which includes the electrical interconnects 438 and the sensor electrodes 440 as shown in FIG. 4Q.

In examples, the second etch mask 466 may be similar to the first etch mask 462. For instance, the partially fabricated device 400*p* may be pre-processed in preparation for forming the second etch mask 466 in the same manner the partially fabricated device 400*m* is pre-processed in preparation for forming the first etch mask 462.

Referring back to FIG. 3, at block 318, the method 300 includes removing the second portion of the second bio-compatible layer, thereby exposing a portion of the second conductive layer. As shown in FIG. 4R, exposed portions 464A, 464B, and 468 of the second bio-compatible layer 458 (i.e., the portions that are not covered by the second etch mask 466) are removed to provide a partially-fabricated device 400*r*. In an example, the exposed portions 464A, 464B, and 468 of the second bio-compatible layer 458 are removed by etching using an inductively coupled plasma at a power for a time period. In some examples, the inductively coupled plasma may include an oxygen plasma. Moreover, in some examples, the power may be 400 W at a 300 W bias. Further, in some examples, the time period may be 33 minutes. And, in such an example, the etching may comprise one or more cycles that comprises an etch period followed by a rest period, such that the partially-fabricated device 400*r* may cool down. In some examples, the etch period may be 3 minutes. Moreover, in some examples, the rest period may be 2 minutes. Further, in some examples, the one or more cycles may be 11 cycles. And, in some examples, the one or more cycles may be applied in sequence. Other plasmas and/or types of plasmas may be used as well, such as a plasma asher, a reactive ion etcher, etc.

The portions 464A and 464B of the second bio-compatible layer 458 (and corresponding portions of the first-bio-compatible layer 410) are etched, such that a portion 470 of the sacrificial layer 404 is exposed. The portion 470 of the sacrificial layer 404 that is exposed may be referred to as a release region. In some examples (not shown), when the portions 464A and 464B of the second bio-compatible layer 458 (and corresponding portions of the first-bio-compatible layer 410) are etched, the portion 470 of the sacrificial layer 404 may be etched as well.

Additionally, etching the portions 464A and 464B of the second bio-compatible layer 458 (and corresponding portions of the first-bio-compatible layer 410) may leave excess material 472. With this approach, the second etch mask 466 may define a shape of the bio-compatible device and/or a shape of the antenna 422.

As shown in FIG. 4R, the portion 468 of the second bio-compatible layer is also removed, while or after removing the portions 464A and 464B, to thereby expose the sensor electrodes 440 to provide the partially-fabricated device 400*r*. Remaining portions of the second etch mask 466 may be removed to provide partially-fabricated device 400*s* shown in FIG. 4S.

As shown in FIG. 4T, the sacrificial layer 404 is removed to release the bio-compatible device 400*t* from the working substrate 402. The sacrificial layer 404 may be removed in a variety of ways. For example, the sacrificial layer 404 may be removed by dissolving the sacrificial layer 404 in a fluid at a temperature for a time period. In some examples, the sacrificial layer 404 may be dissolved in the fluid through the portion 470 of the sacrificial layer 404 that is exposed (or that was etched when the portions 464A and 464B of the second bio-compatible layer 458, and the corresponding portions of the first bio-compatible layer 410, are etched using the inductively coupled plasma). As another example, the sacrificial layer 404 may be removed by etching (e.g., wet etching) using an etchant that might not etch the second bio-compatible layer 458, the first bio-compatible layer 410, and/or the conductive pattern 448.

Moreover, in an example, removal may further involve soaking in a fluid, rinsing with the fluid, and drying. In some examples, the fluid may include DI water. Moreover, in some examples, drying may involve hand drying on a towel.

As illustrated in FIG. 4T, the bio-compatible device 400*t* includes the first bio-compatible layer 410, the antenna 422, the electrical contacts 424, the electrical interconnects 426, the electrical interconnects 438, the sensor electrodes 440, the second bio-compatible layer 458, the first side 412 of the bio-compatible device, and the second side 460 of the bio-compatible device 400*t*. The first bio-compatible layer 410 and the second bio-compatible layer 458 encapsulate the assembled components, except the sensor electrodes 440, which are exposed as shown in FIG. 4T.

The bio-compatible device 400*t* is suitable for incorporation into a biological environment, such as within a body-mountable device or an implantable medical device, for example. Due to the encapsulating bio-compatible material, the surrounding environment is sealed from the embedded components. For example, if the bio-compatible device 400*t* is implanted in a biological host, or placed in an eye-mountable device to be exposed to tear fluid, the bio-compatible device 400*t* is able to be exposed to fluids of the biological host (e.g., tear fluid, blood, etc.), because the entire exterior surface is coated with bio-compatible material, except that the sensor electrodes 440 are exposed to allow detection of one or more analytes in the fluid.

The description in FIGS. 4A-4T describes one example of a process for fabricating a bio-compatible device that can be embedded in an eye-mountable device. However, the process described with reference to FIGS. 4A-4T may be employed to create bio-compatible devices for other applications, such as other mountable devices or implantable electronic medical device applications. Such implantable electronic medical devices may include an antenna for communicating information (e.g., sensor results) and/or inductively harvesting energy (e.g., radio frequency radiation). Implantable electronic medical devices may also include electrochemical sensors or they may include other electronic devices. The process described with reference to FIGS. 4A-4T may be used to create bio-compatible devices suitable to be mounted on or in another part of the body, such as the skin, a tooth, or on a tissue in the mouth, for example.

III. CONCLUSION

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some examples may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A method of making a bio-compatible device, the method comprising:
   forming a first bio-compatible layer, wherein the first bio-compatible layer defines a first side of the bio-compatible device;
   forming a first conductive layer over a portion of the first bio-compatible layer;
   forming a second conductive layer over a portion of the first conductive layer;
   mounting an electronic component to a portion of the first conductive layer not covered by the second conductive layer;
   forming a second bio-compatible layer over the first bio-compatible layer, the electronic component, the first conductive layer and the second conductive layer, wherein the second bio-compatible layer defines a second side of the bio-compatible device;
   forming a first etch mask to partially cover the second bio-compatible layer, thereby exposing a first portion of the second bio-compatible layer;
   removing the first portion of the second bio-compatible layer;
   forming a second etch mask to partially cover the second bio-compatible layer, thereby exposing a second portion of the second bio-compatible layer, wherein the second portion of the second bio-compatible layer covers, at least partially, the second conductive layer; and
   removing the second portion of the second bio-compatible layer, thereby exposing a portion of the second conductive layer.

2. The method of claim 1, further comprising:
   forming a sacrificial layer on a working substrate, wherein the first bio-compatible layer is formed on the sacrificial layer; and
   removing the sacrificial layer.

3. The method of claim 2, wherein removing the sacrificial layer comprises dissolving the sacrificial layer in a fluid.

4. The method of claim 1, wherein forming the first conductive layer comprises:
   forming the first conductive layer such that the first conductive layer has a non-uniform thickness.

5. The method of claim 1, wherein the second conductive layer defines an antenna, sensor electrodes, electrical contacts, and electrical interconnects, and wherein removing the second portion of the second bio-compatible layer exposes the sensor electrodes.

6. The method of claim 1, wherein removing the second portion of the second bio-compatible layer comprises:
   etching, using an inductively coupled plasma, the second portion of the second bio-compatible layer exposed by the second etch mask.

7. The method of claim 1, wherein mounting the electronic component to the portion of the first conductive layer not covered by the second conductive layer comprises:
   bonding the electronic component to the portion of the first conductive layer using anisotropic conductive paste.

8. The method of claim 1, further comprising:
   treating a surface of the first bio-compatible layer, such that a surface of the second bio-compatible layer bonds to the surface of the first bio-compatible layer during formation of the second bio-compatible layer.

9. The method of claim 8, wherein treating the surface of the first bio-compatible layer comprises:
   treating the surface of the first bio-compatible layer with an inductively coupled plasma.

10. A method of making a bio-compatible device, the method comprising:
    forming a first bio-compatible layer, wherein the first bio-compatible layer defines a first side of the bio-compatible device;
    forming a conductive pattern over a portion of the first bio-compatible layer, wherein the conductive pattern defines an antenna, sensor electrodes, electrical contacts, and one or more electrical interconnects;
    mounting an electronic component to the electrical contacts;
    forming a second bio-compatible layer over the first bio-compatible layer, the electronic component, the conductive pattern, wherein the second bio-compatible layer defines a second side of the bio-compatible device;
    forming a first etch mask to partially cover the second bio-compatible layer, thereby exposing a first portion of the second bio-compatible layer;
    removing the first portion of the second bio-compatible layer;
    forming a second etch mask to partially cover the second bio-compatible layer, thereby exposing a second portion of the second bio-compatible layer, wherein the second portion of the second bio-compatible layer covers the sensor electrodes; and removing the second portion of the second bio-compatible layer, thereby exposing the sensor electrodes.

11. The method of claim 10, further comprising:
forming a sacrificial layer on a working substrate, wherein the first bio-compatible layer is formed on the sacrificial layer; and
removing the sacrificial layer.

12. The method of claim 11, wherein the sacrificial layer comprises at least one metal layer that adheres to the working substrate.

13. The method of claim 11, wherein the sacrificial layer further comprises at least one metal layer that bonds to the first bio-compatible layer.

14. The method of claim 11, wherein removing the sacrificial layer comprises dissolving the sacrificial layer in a fluid.

15. The method of claim 10, wherein forming the conductive pattern comprises:
forming a first conductive layer over a portion of the first bio-compatible layer such that the first conductive layer has a non-uniform thickness, wherein the first conductive layer defines the antenna, the electrical contacts, and at least one of the one or more electrical interconnects; and forming a second conductive layer over a portion of the first conductive layer, wherein the second conductive layer defines the sensor electrodes and at least one of the one or more electrical interconnects.

16. The method of claim 15, wherein forming the conductive pattern over the portion of the first bio-compatible layer comprises:
forming a seed layer over the first bio-compatible layer;
forming a first sacrificial layer over a portion of the seed layer;
forming the first conductive layer over portions of the seed layer not covered by the first sacrificial layer;
removing the first sacrificial layer;
removing portions of the seed layer not covered by the first conductive layer;
forming a second sacrificial layer over a portion of the first bio-compatible layer and a portion of the first conductive layer;
forming the second conductive layer over portions of the first conductive layer not covered by the second sacrificial layer; and
removing the second sacrificial layer.

* * * * *